(12) United States Patent
Gaur et al.

(10) Patent No.: US 9,827,129 B2
(45) Date of Patent: Nov. 28, 2017

(54) METHODS AND DEVICES FOR DEPLOYING AND RELEASING A TEMPORARY IMPLANT WITHIN THE BODY

(71) Applicant: Allurion Technologies, Inc., Wellesley, MA (US)

(72) Inventors: Shantanu K. Gaur, Canonsburg, PA (US); Samuel G. Levy, Paris (FR); Jonathan Wecker, Weston, MA (US); Bruce A. Horwitz, Newton, MA (US); Jinyoung Daniel Gwak, San Francisco, CA (US)

(73) Assignee: Allurion Technologies, Inc., Natick, MA (US)

( * ) Notice: Subject to any disclaimer, the term of this patent is extended or adjusted under 35 U.S.C. 154(b) by 0 days.

(21) Appl. No.: 15/174,864

(22) Filed: Jun. 6, 2016

(65) Prior Publication Data

US 2016/0278957 A1    Sep. 29, 2016

Related U.S. Application Data

(63) Continuation of application No. 14/301,210, filed on Jun. 10, 2014, now Pat. No. 9,387,107, which is a continuation of application No. 13/773,516, filed on Feb. 21, 2013, now Pat. No. 8,870,907.

(60) Provisional application No. 61/601,384, filed on Feb. 21, 2012, provisional application No. 61/762,196, filed on Feb. 7, 2013, provisional application No. 61/645,601, filed on May 10, 2012, provisional application No. 61/647,730, filed on May 16, 2012, (Continued)

(51) Int. Cl.
*A61M 29/00* (2006.01)
*A61F 5/00* (2006.01)

(52) U.S. Cl.
CPC .............. *A61F 5/003* (2013.01); *A61F 5/004* (2013.01); *A61F 5/0036* (2013.01); *A61F 5/0043* (2013.01); *A61F 5/0089* (2013.01)

(58) Field of Classification Search
CPC ...... A61F 5/0003; A61F 5/0013; A61F 5/003; A61F 5/0033; A61F 5/0036; A61F 5/0043; A61F 5/0073
USPC ........................................ 606/192; 623/23.65
See application file for complete search history.

(56) References Cited

U.S. PATENT DOCUMENTS

| 3,853,116 A | 12/1974 | Bucalo |
| 4,133,315 A | 1/1979 | Berman et al. |

(Continued)

FOREIGN PATENT DOCUMENTS

| WO | WO 00/12167 | 3/2000 |
| WO | WO 2006/020929 | 2/2006 |

(Continued)

OTHER PUBLICATIONS

U.S. Appl. No. 14/301,210, filed Jun. 10, 2014.
U.S. Appl. No. 13/901,338, filed May 23, 2013.
U.S. Appl. No. 13/773,516, filed Feb. 21, 2013.

*Primary Examiner* — Diane Yabut
*Assistant Examiner* — Martin T Ton
(74) *Attorney, Agent, or Firm* — Levine Bagade Han LLP

(57) ABSTRACT

Methods, devices and systems for delivering a device assembly into a gastric or other space within the body, allowing the device to expand to occupy volume within the gastric space and, after an effective period of time, delivering a substance or stimulus to begin breakdown of the expanded device so that it may release from the body.

22 Claims, 20 Drawing Sheets

Related U.S. Application Data provisional application No. 61/663,433, filed on Jun. 22, 2012, provisional application No. 61/663,682, filed on Jun. 25, 2012, provisional application No. 61/663,683, filed on Jun. 25, 2012, provisional application No. 61/674,126, filed on Jul. 20, 2012, provisional application No. 61/699,942, filed on Sep. 12, 2012.

(56) References Cited

U.S. PATENT DOCUMENTS

| | | | |
|---|---|---|---|
| 4,723,547 A * | 2/1988 | Kullas | A61F 5/0036 604/909 |
| 4,899,747 A | 2/1990 | Garren et al. | |
| 4,949,756 A | 8/1990 | Melinyshyn et al. | |
| 5,348,537 A | 9/1994 | Wiesner et al. | |
| 5,595,521 A | 1/1997 | Becker | |
| 5,950,624 A | 9/1999 | Hart | |
| 6,259,953 B1 | 7/2001 | Lucchesi et al. | |
| 6,375,972 B1 | 4/2002 | Guo et al. | |
| 6,712,832 B2 | 3/2004 | Shah | |
| 7,485,093 B2 | 2/2009 | Glukhovsky | |
| 7,854,745 B2 | 12/2010 | Brister et al. | |
| 8,202,291 B1 | 6/2012 | Brister et al. | |
| 8,287,562 B2 | 10/2012 | Kasic, II | |
| 8,292,911 B2 | 10/2012 | Brister et al. | |
| 8,814,898 B2 | 8/2014 | Gaur et al. | |
| 8,870,907 B2 | 10/2014 | Gaur et al. | |
| 8,974,483 B2 | 3/2015 | Gaur et al. | |
| 9,662,239 B2 | 5/2017 | Brister et al. | |
| 2003/0229384 A1 | 12/2003 | Mon | |
| 2004/0146559 A1 | 7/2004 | Sowden et al. | |
| 2005/0055039 A1 | 3/2005 | Burnett et al. | |
| 2007/0078476 A1 | 4/2007 | Hull, Sr. et al. | |
| 2008/0195226 A1 | 8/2008 | Williams et al. | |
| 2008/0241094 A1 | 10/2008 | Burnett et al. | |
| 2008/0243071 A1 | 10/2008 | Quijano et al. | |
| 2008/0249635 A1 | 10/2008 | Weitzner et al. | |
| 2009/0024227 A1 | 1/2009 | Lesh | |
| 2009/0048684 A1 | 2/2009 | Lesh | |
| 2009/0192535 A1 * | 7/2009 | Kasic, II | A61F 5/0036 606/157 |
| 2009/0259246 A1 | 10/2009 | Eskaros et al. | |
| 2010/0062057 A1 | 3/2010 | Berge et al. | |
| 2010/0100116 A1 | 4/2010 | Brister et al. | |
| 2010/0121224 A1 | 5/2010 | Toyota et al. | |
| 2010/0137897 A1 * | 6/2010 | Brister | A61F 5/003 606/192 |
| 2010/0174307 A1 | 7/2010 | Birk | |
| 2011/0112383 A1 | 5/2011 | Voss et al. | |
| 2012/0141544 A1 | 6/2012 | Fuisz et al. | |
| 2012/0141545 A1 | 6/2012 | Fuisz et al. | |
| 2012/0232576 A1 | 9/2012 | Brister et al. | |
| 2013/0035711 A1 | 2/2013 | Schwab et al. | |
| 2013/0218190 A1 | 8/2013 | Gaur et al. | |
| 2013/0267984 A1 | 10/2013 | Gaur et al. | |
| 2013/0296751 A1 | 11/2013 | Martin et al. | |
| 2014/0066967 A1 | 3/2014 | Levy et al. | |
| 2014/0296903 A1 | 10/2014 | Gaur et al. | |
| 2015/0196408 A1 | 7/2015 | Moss et al. | |

FOREIGN PATENT DOCUMENTS

| | | |
|---|---|---|
| WO | WO 2009/059802 | 5/2009 |
| WO | WO 2011/106157 | 9/2011 |
| WO | WO 2013/126593 | 8/2013 |
| WO | WO 2014/074625 | 5/2014 |

* cited by examiner

METHODS AND DEVICES FOR DEPLOYING AND RELEASING A TEMPORARY IMPLANT WITHIN THE BODY

CROSS-REFERENCE TO RELATED APPLICATIONS

This application is a continuation of U.S. patent application Ser. No. 14/301,210, filed Jun. 10, 2014, now U.S. Patent No. 9,387,107 which is a continuation of U.S. patent application Ser. No. 13/773,516 filed Feb. 21, 2013, now U.S. Pat. No. 8,870,907, which is a non-provisional of U.S. Provisional Applications Nos.: No. 61/762,196 entitled Thermally Degradable Biocompatible Constructs and Methods of Degrading filed Feb. 7, 2013; 61/601,384 entitled Swallowed Intragastric Balloon Filled via Narrow Extracorporeal Tube filed Feb. 21, 2012; 61/645,601 entitled Delivery String for Gastrointestinal Applications filed May 10, 2012; 61/647,730 entitled Hydrogel Driven Valve filed May 16, 2012; 61/663,433 entitled Fluid Transfer Device for Hydrogel Constructs filed Jun. 22, 2012; 61/663,682 entitled Hydrogel Driven Valve filed Jun. 25, 2012; 61/663,683 entitled Fluid Transfer Device for Hydrogel Constructs filed Jun. 25, 2012; No. 61/674,126 entitled Payload Delivery System and Method filed Jul. 20, 2012; and 61/699,942 entitled System for Rapid Hydrogel Construct Degradation filed Sep. 12, 2012, the entirety of each of which is incorporated by reference.

BACKGROUND OF THE INVENTION

The present invention generally relates to the field of devices that temporarily occlude spaces within the body to provide a therapeutic effect.

According to 2010 World Health Organization data, 198 million Americans over the age of 15 are above target weight. Of these individuals, 89 million are considered overweight (25<Body Mass Index<30) and 109 million are considered obese (Body Mass Index>30). Worldwide, more than 1.4 billion adults age 20 and over are overweight, and 500 million are obese. Obesity places patients at increased risk of numerous, potentially disabling conditions including type 2 diabetes, heart disease, stroke, gallbladder disease, and musculoskeletal disorders 1,2,3. Compared with healthy weight adults, obese adults are more than three times as likely to have been diagnosed with diabetes or high blood pressure4. In the United States it is estimated that one in five cancer-related deaths may be attributable to obesity in female non-smokers and one in seven among male non-smokers (>=50 years of age). On average, men and women who were obese at age 40 live 5.8 and 7.1 fewer years, respectively, than their healthy weight peers.

Gastric bypass surgery is the current gold standard treatment for patients with a body mass index ("BMI") of greater than 40. Gastric bypass surgery is also an option for those with a BMI between 35-39 with obesity-related co-morbidities. While gastric bypass surgery results in decreased food consumption and weight loss for a majority of recipients, it requires life-altering, permanent anatomic modifications to the gastrointestinal tract and can result in severe complications. Gastric bypass and related surgical procedures are also expensive, costing about $22,500 (by laparoscopy). For these reasons, only about 250,000 surgical obesity procedures are performed per year in the US.

For the vast majority of the overweight and obese population for whom surgical obesity procedures are not appropriate, few efficacious and affordable interventions are currently available. Diet and exercise remain the front line approaches to obesity, however this approach has at best slowed the growth of the epidemic. To date, drug therapies have dose limiting side effects or have lacked meaningful long term efficacy.

One less-invasive intervention that has begun to gain popularity is an intragastric balloon. Intragastric balloons can be placed endoscopically or positioned using other methods and generally must be removed endoscopically or rely on the body's natural digestive processes for removal.

The devices, methods, and systems discussed herein are intended to provide an effective treatment for obesity. Moreover, the devices, methods, and systems described herein are not limited to any particular patient population and can even be applied to clinical areas outside of obesity.

SUMMARY OF THE INVENTION

The present invention relates to devices and methods for occupying a space within a patient's body. In particular, the devices and methods can be used within a gastric space. However, the devices and methods can be used in any part of the body.

In a first example, a medical device under the present disclosure includes a device assembly comprising a skin, a fluid transfer member, and a release material, the skin forming a perimeter of the device assembly defining a reservoir therein, where the release material is coupled to at least a portion of the skin such that the skin and release material are coupled to create a physical barrier about the reservoir, where the skin is liquid impermeable and where the fluid transfer member permits delivery of fluids into the reservoir through the physical barrier; the device assembly having a deployment profile and an active profile, where the deployment profile is smaller than the active profile and permits deployment of the device assembly within a gastric space in the patient's body; a filler material retained within the reservoir by the physical barrier and configured to expand as fluid is delivered through the fluid transfer member to cause the device assembly to expand from the deployment profile to the active profile such that the device assembly occupies at least a portion of the gastric space within the patient's body; wherein exposure of the release material to an exogenous substance opens at least one path in the physical barrier such that the filler material can pass into the patient's body resulting in reduction of a size of the deployment profile. As noted herein, an exogenous material, substance, and/or stimuli as used herein can comprise any material or substance that is not normally found within the patient's body (or has a condition not normally found within the patient's body, including duration). In most cases the exogenous material, substance and/or stimuli originate from outside the patient's body. In many variations, such an exogenous trigger allows for control over the duration of time that the device is located within the body. In some variations, the exogenous material is the fluid used to fill the reservoir initially (for example, a fluid with a certain osmolality). One such benefit is that, as body chemistry varies between populations of potential patients, the use of exogenous triggers reduces the variability of the duration of device placement and improve patient outcomes as a result of the devices, methods, and systems that rely on such exogenous triggers.

Variations of the devices and methods herein can include two possible manifestations: a) the degradation occurs over time but is exquisitely controlled by choice of filler fluid and release material and the initial conditions inside the device;

and/or b) the degradation occurs on-demand via introduction of exogenous stimulus following deployment.

The fluid transfer member can include any number of components from a simple orifice in a skin of the device, to a conduit or wick member. The fluid transfer member can also optionally include a sealable fluid path.

In another variation of the device, the fluid transfer member further comprises a conduit having a proximal end and a device end, where the device end of the conduit is flexible to accommodate swallowing by the patient and the conduit is coupled to the sealable fluid path, where a length of the conduit permits delivery of fluid into the reservoir when the device assembly is located within the patient's body and the proximal end is positioned outside of the patient's body. The device can also include a conduit that is detachable from the sealable fluid path when pulled away from the sealable path, wherein the sealable path is configured to form an effective seal upon removal of the conduit.

In certain variations, the sealable fluid path is configured to collapse to be substantially sealed when the device assembly assumes the active profile and the conduit is detached from the sealable fluid path.

An additional variation of the device further comprises an elongated? conduit having a proximal end and a device end, where the device end is flexible to accommodate swallowing by the patient, where the sealable fluid path comprises a flexible elongate tunnel extending from the reservoir to an exterior of the skin, where the device end of the conduit is removably located within the flexible elongate tunnel structure, such that upon removal of the conduit the flexible elongate tunnel structure increases a resistance to movement of substances there through to form a seal.

Fluid transfer members described herein can further comprise a wick element where a first end of the wick element is in fluid communication with the reservoir and a second end of the wick element extends out of the sealable fluid path such that when positioned within the stomach of the patient, the wick draws fluid from the stomach of the patient into the reservoir.

In some variations, the fluid path is configured to compress the wick element to seal the fluid path as the device assembly assumes the active profile. In additional variations, the wick element withdraws into the reservoir as the device assembly assumes the active profile such that the fluid path seals as the filler material expands within the reservoir.

Variations of the device include skins having at least one opening and where each of the at least one openings are covered by the release material. For example, the release material can comprise a plurality of discrete portions covering a plurality of openings in the skin. At least a portion of the release material can optionally comprise a shape that approximates a shape of the deployment profile, reducing the amount of deformation of the release material.

In additional variations, a portion of the skin defining an opening is mechanically bound together by a portion of the release material to close the physical barrier. For example, in certain embodiments at least two edges of the skin are located on an interior of the device assembly.

Devices of the present disclosure can include one or more release material(s) located on an interior of the reservoir such that the release material is physically separated from bodily fluids.

The filler material used in any of the devices or methods disclosed herein can comprise, when expanded, a semi-solid consistency similar to natural substances within the body.

The present disclosure also includes methods for temporarily occupying space in a body of a patient, such as in a gastric region or other area of the body. Such a method can include providing a device assembly having a conduit comprising a flexible end portion free of rigid and/or semi-rigid materials to enable swallowing of the device assembly and the flexible end portion, where the flexible end portion has an end that extends within a reservoir of the device assembly; deploying the device assembly within the gastric space (where deploying can optionally include directing or inducing a patient to swallow the device); delivering a fluid through the supply tube such that the device assembly expands to an active profile that occupies a sufficient volume within the gastric space to provide a therapeutic effect; and withdrawing the supply tube from the device assembly allowing the device assembly to self seal and permit the device assembly to remain within the gastric space for a period of time. In some variations, deploying the device includes directing a patient to swallow the device assembly while optionally maintaining control of the proximal end of the conduit outside the body.

The method described herein can also include a device assembly that further comprises a liquid impermeable skin material that is coupled to a release material to form a physical barrier, the method further comprising delivering an exogenous substance to the gastric space that causes disruption of the release material and allows the device assembly to reduce in size.

The exogenous substance can optionally comprise a fluid having a temperature greater than body temperature. The exogenous substance can optionally comprise a material that raises a temperature within the gastric space, which causes disruption of the release material. In additional variations, the exogenous substance can be present in the filler fluid, often with the intention of causing a predicted but time-delayed trigger of the release material.

In another variation of the method, the device assembly further comprises a filler material within the reservoir that expands when combined with the fluid, where delivering the fluid comprises delivering the fluid until the combination of fluid and filler material expands the device assembly to the active profile.

Another variation of the method includes deploying a plurality of device assemblies such that the plurality of device assemblies occupies a volume to provide the therapeutic effect.

In an additional variation, a method for temporarily occupying a space in a body of a patient can include: providing a device assembly having a hydroscopic member extending from an exterior of the device assembly into a reservoir of the device assembly, a filler material located within the reservoir where the device assembly and hydroscopic member are capable of being swallowed by the patient; wherein after positioned within the gastric space, the hydroscopic member absorbs fluids within the gastric space and delivers the fluids into the reservoir such that the fluids combine with the filler material to expand the device assembly into an active profile until the device assembly self-seals; and delivering a substance to the gastric space to cause a portion of the device assembly to degrade and allow the expanded filler material to escape from the reservoir and pass within the body of the patient.

Another variation of a device of the present disclosure can include a device assembly comprising a skin, a fluid transfer member, the skin forming a perimeter of the device assembly defining a reservoir therein, where the skin is liquid impermeable and where the fluid transfer member comprises a flexible elongate fluid path that permits delivery of fluids into the reservoir; the device assembly having a deployment profile and an active profile, where the deployment profile is smaller than the active profile and permits positioning of the device assembly within the patient's body via swallowing of the device assembly; a filler material retained within the reservoir and configured to expand as fluid is delivered through the fluid transfer member to cause the device assembly to expand from the deployment profile to the active profile such that the device assembly occupies at least a portion of the gastric space within the patient's body; and an elongate conduit having a proximal end and a device end, where the device end is flexible to accommodate swallowing by the patient, the elongate conduit configured to deliver fluid through the fluid transfer member, where the device end of the conduit is removably located within the flexible elongate fluid path, such that upon removal of the conduit the flow resistance of the flexible elongate fluid path is sufficient to prevent filler material from escaping.

In another variation, a medical device for occupying a space within a patient's body comprises a device assembly comprising a skin, a fluid transfer member, and a release material, the surface layer forming a perimeter of the device assembly defining a reservoir therein, where the release material is coupled to at least a portion of the skin such that the skin and release material form a physical barrier about the reservoir and where the fluid transfer member comprises a flexible elongate valve extending within the reservoir; a conduit having a proximal end extending from outside of the perimeter of the device assembly and a flexible device end extending through flexible elongate valve, the flexible device end having a compliance to permit swallowing of the device end and device assembly; a filler material retained within the reservoir by the physical barrier and configured to expand as fluid is delivered through the fluid transfer member to cause the device assembly to expand from a deployment profile to an active profile such that the device assembly occupies at least a portion of the gastric space within the patient's body in the active profile; wherein the conduit device end is removable from the flexible elongate valve upon assuming the active profile, wherein upon removal of the device end from the flexible elongate valve, a flow resistance of the flexible elongate valve prevents filler material from escaping therethrough; and wherein exposure of the release material to a substance not naturally produced in the body disrupts the release material in a predictable manner and opens at least one path in the physical barrier.

Another variation of a medical device for occupying a gastric space within a patient's body comprises: a device assembly comprising a skin and a fluid transfer member, the surface layer forming a perimeter of the device assembly defining a reservoir therein; a conduit having a proximal end extending outside of the perimeter of the device assembly and a device end extending through the fluid transfer member such that the conduit is in fluid communication with the reservoir, wherein the conduit comprises a hydroscopic material that pulls fluid from the gastric space into the reservoir; and a filler material retained within the reservoir by the physical barrier and configured to expand as fluid is delivered through the fluid transfer member to cause the device assembly to expand from a deployment profile to an active profile such that the device assembly occupies at least a portion of the gastric space within the patient's body in the active profile, wherein in the active profile the expanded filler material causes closure of the fluid transfer member to prevent the conduit from pulling fluid into the reservoir.

In yet another variation, the entire skin can comprise a release material such that an exogenous trigger causes disruption of the entire device to begin the breakdown process.

Another variation of a device for occupying a space within a patient's body includes a device assembly comprising a skin, a fluid transfer member, and a release material, the skin forming a perimeter of the device assembly defining a reservoir therein, where the release material is coupled to at least a portion of the skin such that the skin and release material are coupled to create a physical barrier about the reservoir, where the skin is liquid impermeable and where the fluid transfer member permits delivery of fluids into the reservoir through the physical barrier; the device assembly having a deployment profile and an active profile, where the deployment profile is smaller than the active profile and permits deployment of the device assembly within a gastric space in the patient's body; whereupon fluid entering the reservoir causes the device assembly to expand from the deployment profile to the active profile such that the device assembly occupies at least a portion of the gastric space within the patient's body; and wherein application of an exogenous substance opens at least t one path in the physical barrier such the fluids exit the reservoir resulting in reduction of a size of the deployment profile.

The devices described herein can also be used for delivery of drugs, pharmaceuticals, or other agents where such items can be delivered on a skin of the device, within a reservoir, in a filler of the device, or anywhere on the device. Such agents can be released over time.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

The foregoing and other objects, features and advantages of the methods, devices, and systems described herein will become apparent from the following description in conjunction with the accompanying drawings, in which reference characters refer to the same parts throughout the different views. The drawings are not necessarily to scale; emphasis has instead been placed upon illustrating the principles of the invention. Of the drawings.

DETAILED DESCRIPTION OF THE INVENTION

The following illustrations are examples of the invention described herein. It is contemplated that combinations of aspects of specific embodiments or combinations of the specific embodiments themselves are within the scope of this disclosure. While the methods, devices, and systems described herein are discussed as being used in the stomach or gastric space, the devices, methods, and systems of the present disclosure can be can be used in other parts of the body where temporary occlusion of a space might be required or beneficial. The present disclosure is related to commonly assigned US Publication No. 2011/0295299 filed Mar. 2, 2011 and PCT/US2013/027170, the entirety of both which are incorporated by reference.

Figure 1A:
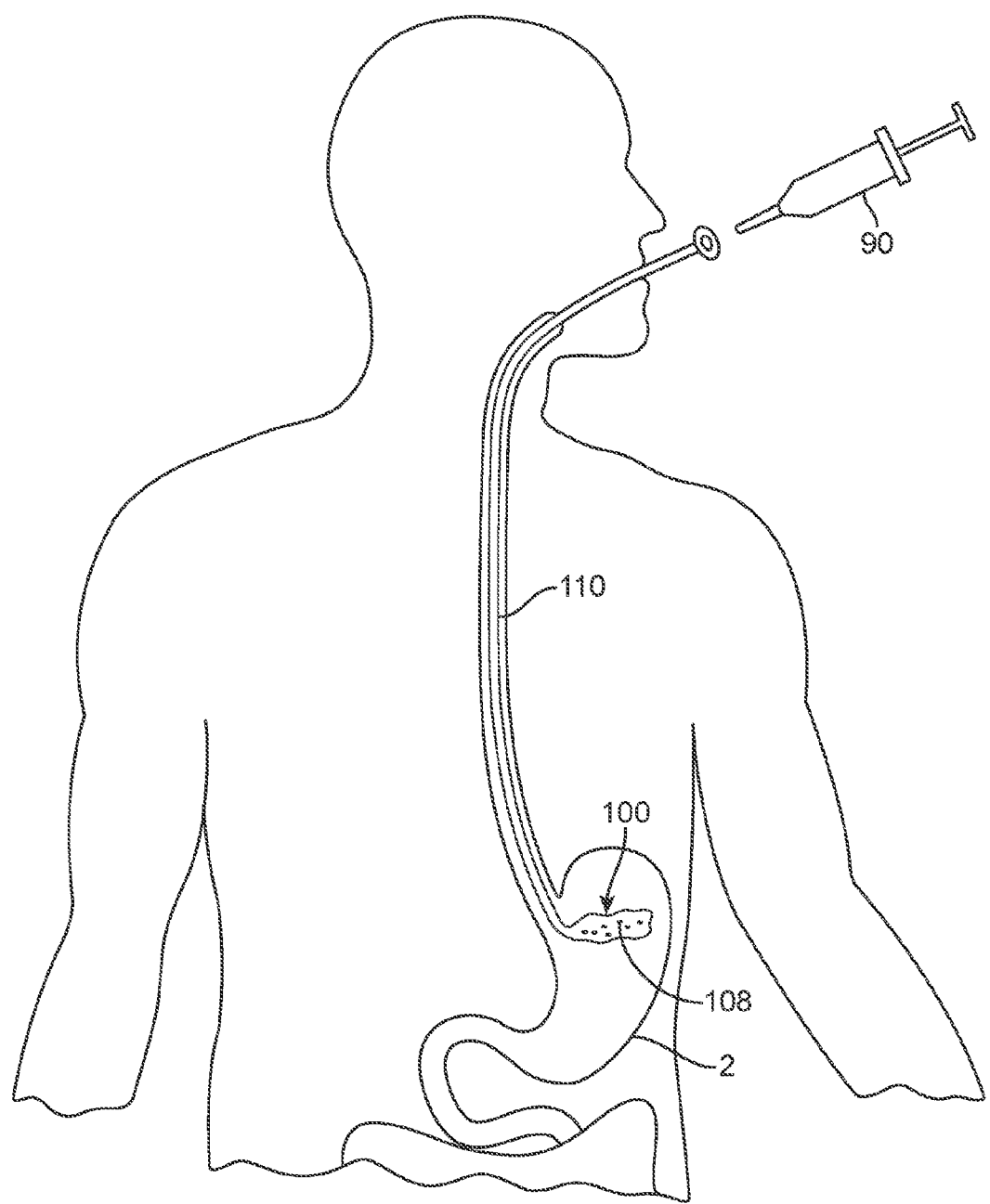
FIG. 1A, illustrates an example of a gastric device assembly prior to assuming an active profile.

FIG. 1A, illustrates an example of a gastric device assembly 100. In this example, the gastric device assembly or construct 100 can reside in a stomach (typically of a mammal) for an extended period of time. One benefit of such a device is that, when partially or fully deployed, the construct 100 occupies volume within the stomach to produce a therapeutic effect, e.g., to stimulate the sensation of satiety, and resists passage from the body by normal body function. As illustrated below the construct generally comprises three states: a pre-deployment configuration (FIG. 1A); a deployed or active configuration (FIG. 1D, 1E); and a release configuration (FIG. 1F). As noted above, the device can also be used for therapeutic benefits that do not involve occupying volume (e.g., drug delivery, creation of a cavity by separating adjacent tissue, etc.).

FIG. 1A illustrates a variation of the device 100 after placement within a stomach 2. As described herein, the initial configuration of the device 100 includes a compact state that allows placement within the body. The device can be in a pill-type configuration or any other shape that permits swallowing. Alternatively, the device 100 can be positioned by the use of a scope type device, catheter, or other medical positioning device.

For a device used in the digestive tract/gastric space, the device assembly 100 can be positioned within the body either by natural ingestion or the use of a delivery system (such as a catheter, endoscope, or other medical device). The delivery system can optionally comprise an oral dosage form, not illustrated, which facilitates the ingestion of a relatively large object. In other embodiments the system comprises a tether that allows manipulation or control of the placed construct from outside of the body. The assembly 100 can also be placed in the stomach by more invasive surgical or endoscopic procedures.

In FIG. 1A, the device 100 is shown immediately after being deployed within the stomach 2 and is ready to be activated. As noted herein, the device 100 can be deployed in the configuration shown. Alternatively, the device can be contained within a capsule or pill-type casing that allows for swallowing by a patient. Once swallowed, the casing will readily dissolve or break down resulting in the configuration shown. Once in place in the stomach, the assembly 100 begins to expand in order to occupy volume/space within the body. Expansion can occur via manual inflation, including hydration or other activation of a filler material (as shown optionally using a catheter, inflation tube or other delivery system), via absorption of body fluids, via remote actuation of a substance already located within the device assembly, and/or delivering of a fluid into the assembly, where the fluid itself causes expansion. Variations of the device also include a combination of such expansion means.

The variation shown in FIG. 1A includes a member 110 that extends from the device 100 to outside of the patient. In this variation shown, the member 110 comprises a fluid transport member that is fluidly coupled to an interior of the device 100 allowing for the delivery of substances and/or fluids within the device 100. FIG. 1A shows an exemplary fluid source 90 coupleable to a variation of a fluid transport member 110 such that the delivery of fluid causes a filler material 108 within the device to expand. In the illustrated example, the fluid transport member comprises a conduit. However, alternate variations of the devices described herein include fluid transport members that reside within the patient's body. Alternate variations of the device 100 also include members 110 that function as delivery or positioning systems to ensure proper placement of the device 100 within the body. Such delivery systems may or may not be fluidly coupled with an interior of the device. In variations discussed below, the device can include one or more fluid transport members that remain within the body but still convey fluid into the device 100 to allow the device to assume an active profile.

Figure 1B:
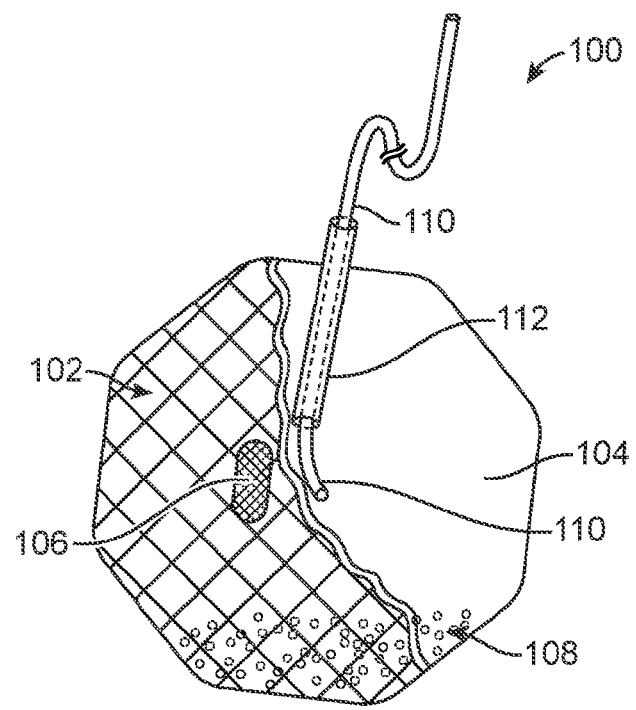
FIGS. 1B and 1C show partial cutaway views of examples of device assemblies for use in occupying space within a body.

FIG. 1B shows one a partial cutaway view of an example of a device assembly 100 for use in occupying space within a body. In this variation, the device assembly 100 includes a material surface or skin 102 that forms a reservoir or pocket 104 capable of retaining a variety of substances, including but not limited to fluids, solid substances, semi-solid substances, etc. In the illustrated variation, the reservoir 104 holds a filler material 108 such as dehydrated hydrogel granules that can swell in size upon the addition of a fluid. However, any number of substances can be contained within the reservoir 104. Alternate variations of the device and/or method include assemblies that do not include a filler material; rather a filler material can be deposited within the reservoir 104 once the assembly is deployed. Alternatively, or in combination, the reservoir can be filled with a gas, liquid or other gel type substance.

In other variations, the device assembly 100 can include an empty reservoir that can be deployed into the body and subsequently filled with a filler material or other substance. For example, such variations can include a liquid filler material that is delivered to the reservoir through a conduit. The volume of liquid required to expand the device into a desired active profile can pre-determined. In some variations, the volume can be determined by measuring the back pressure in the conduit or pressure within the reservoir using any number of pressure detecting elements.

FIG. 1B also illustrates a variation of a sealable fluid path 112 coupled to and/or forming part of the fluid transfer member. In this example, the sealable fluid path 112 extends outside of the perimeter of the skin 102 of the device 100. Additional variations of the device 100 can include significantly shortened sealable fluid paths 112. In yet additional variations, the device assembly 100 can omit the sealable fluid path 112.

As noted herein, the skin 102 includes a release material 106 coupled thereto, where the release material 106 allows for initiating release of the assembly 100 from the body shortly after degradation, activation, or breakdown of the release material. Once the device assembly 100 is in the active profile, it can remain in the active profile for a pre-determined amount of time or until the patient experiences a desired therapeutic effect. To initiate release of the device assembly 100 from the body, an exogenous material, substance or stimulus is administered to the patient. The substance can comprise a fluid or other activating agent having properties that either directly or indirectly act on the release material to disrupt the barrier and allow the contents of the reservoir to be exposed to the body. For example, the exogenous substance can comprise a heated fluid that melts the release material. Alternatively, the exogenous material can change a temperature and/or an acidity of fluids in the stomach such that the enhanced properties of the fluids begin to act, either directly or indirectly, upon the release materials. In additional variations, the release material can comprise a material or materials that effectively form a barrier as discussed herein and are separated or disengaged by the use of an exogenous stimuli (e.g., a magnetic field, ultrasound, IR heating, coherent light, electromagnetic signals, microwave field, etc.).

FIG. 1B also illustrates a variation where the release material 106 is in the form that approximates shape and/or size of the casing used to deliver the device 100 (in this example the release material 106 is in a pill shape). One benefit of such a configuration is that the release material 106 can be positioned within the casing without excessive folding or bending.

Figure 1C:
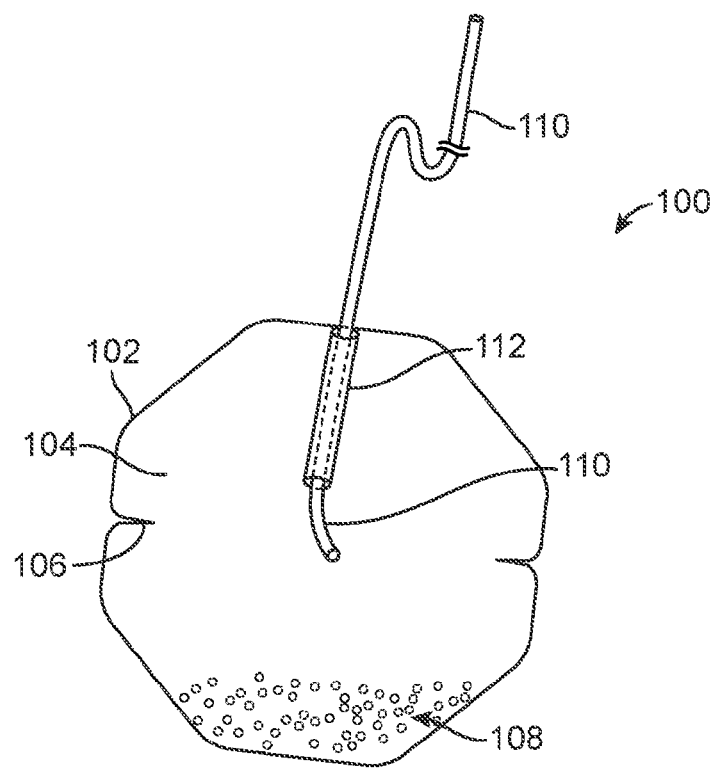

FIG. 1C illustrates a sectional view of another variation of a device assembly 100. In this variation, the release material 106 binds or otherwise joins edges of the skin from within the reservoir 104. Such a configuration protects the release material 106 from the local environment of the body (e.g., fluids within the stomach or digestive tract). The release material can still be activated and/or degraded by the addition of the exogenous material to the body as described herein. However, positioning of the release material within the reservoir permits the skin 102 to serve as an additional layer of protection to prevent inadvertent release of the device assembly 100. The release material 106 can comprise a layer that binds edges of the skin together.

FIG. 1C also illustrates a variation of a sealable fluid path 112. In this example, the sealable fluid path 112 does not extend outside of the perimeter of the skin 102. Additional variations of the device 100 can include significantly shortened sealable fluid paths 112. In yet additional variations, the device assembly 100 can omit the sealable fluid path 112.

Figure 1D:
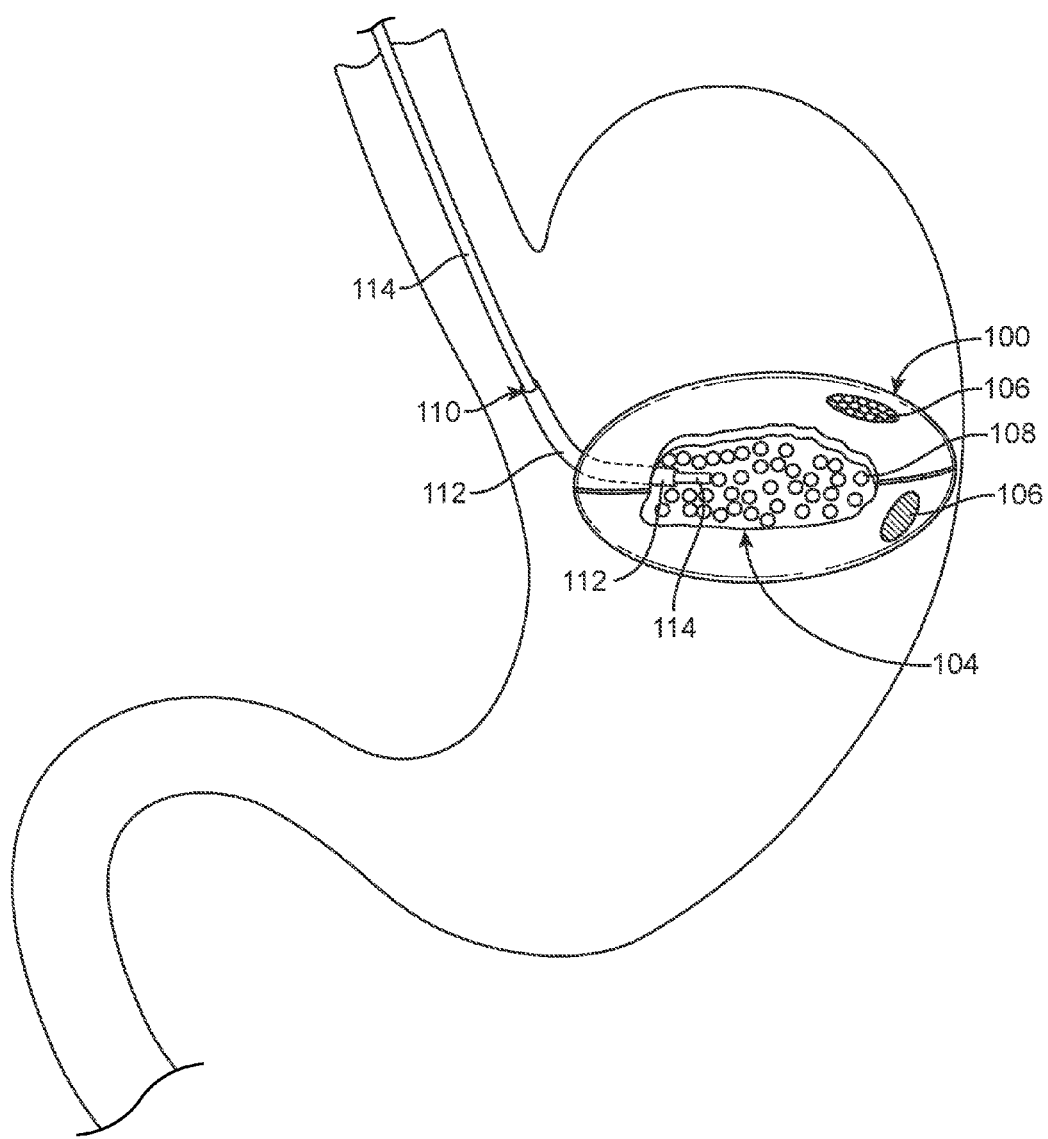
FIG. 1D illustrates the variation of the device shown in FIG. 1A as the device assembly assumes an active profile.

FIG. 1D illustrates the variation of the device 100 shown in FIG. 1A as the device assembly 100 assumes an active profile. An active profile includes any profile apart from a deployment state and where the profile allows the device to perform the intended effect of occupying volume or space within the body to produce a therapeutic effect. In the illustrated example, a physician or other medical practitioner delivers fluid via the fluid transport member 110, comprising a conduit 114 in this variation, and into the reservoir 104 causing a filler material 108 to swell. As noted herein, other variations include device assemblies without filler material where the conduit 114 simply delivers fluid and or other substances that allow the device assembly to achieve an active profile.

When using a conduit 114 that extends outside of the body, a physician can deliver a hydrating liquid, such as water or distilled water through the conduit 114. Generally, a pre-determined volume of liquid can be manually or mechanically pumped into the exterior end of the conduit wherein the volume of liquid is pre-determined based on a particular size of the device assembly or based on a desired active state. In some variations, the volume of liquid can also depend on the length of conduit.

The conduit 114 can be used to transfer a substance or into the reservoir 1014 of the device. In the illustrated variation, the conduit 114 transfers fluid from outside of the patient's body into the reservoir 104 after deployment of device assembly 100 within the body. Alternatively, or in combination, a fluid transfer member can comprise a wick type device that transfers liquids or other fluids from within the body to the reservoir.

Figure 1E:
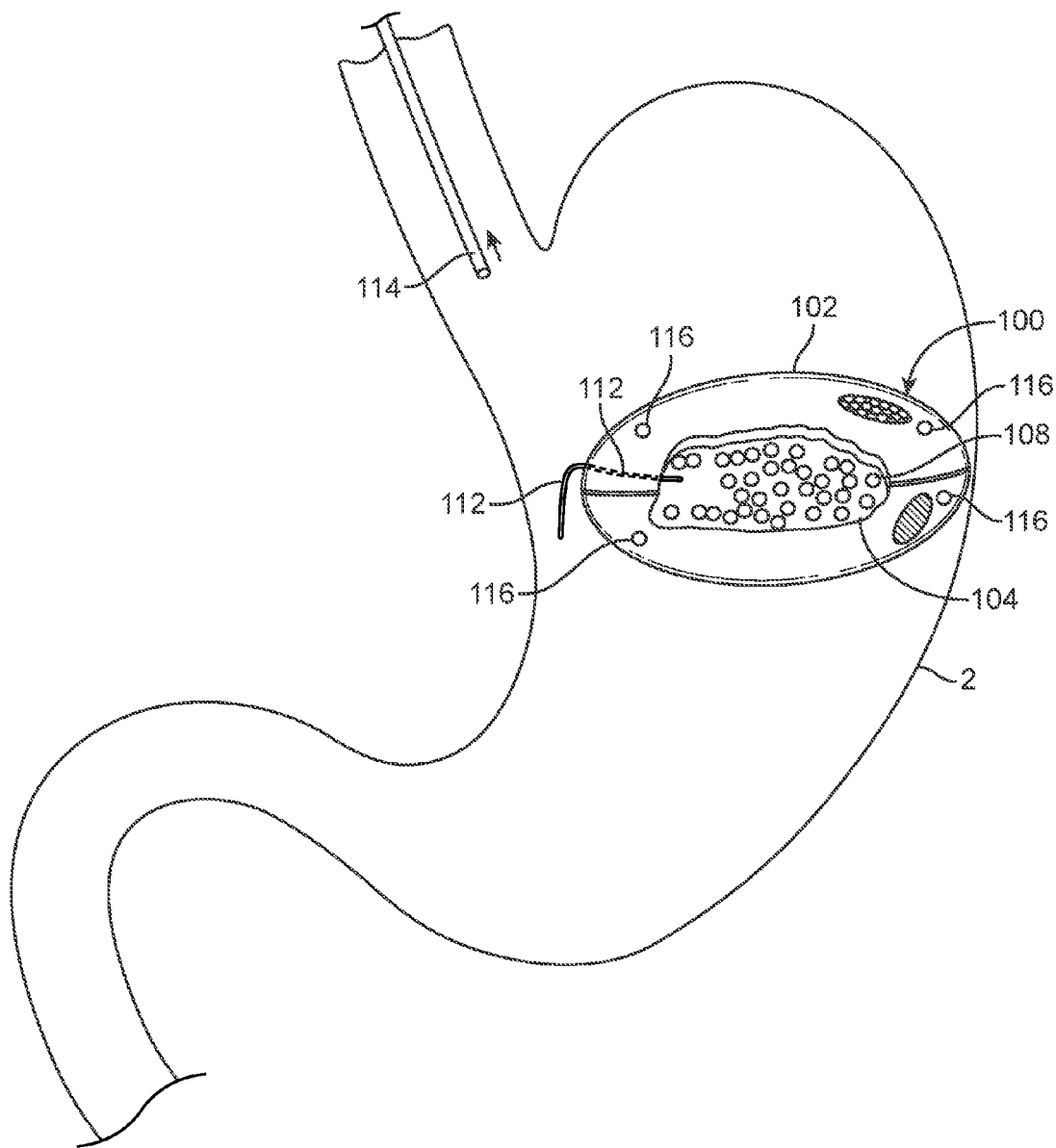
FIG. 1E shows a device assembly after it is inflated, expanded, or otherwise transitioned to achieve a desired active profile.
Figure 1F:
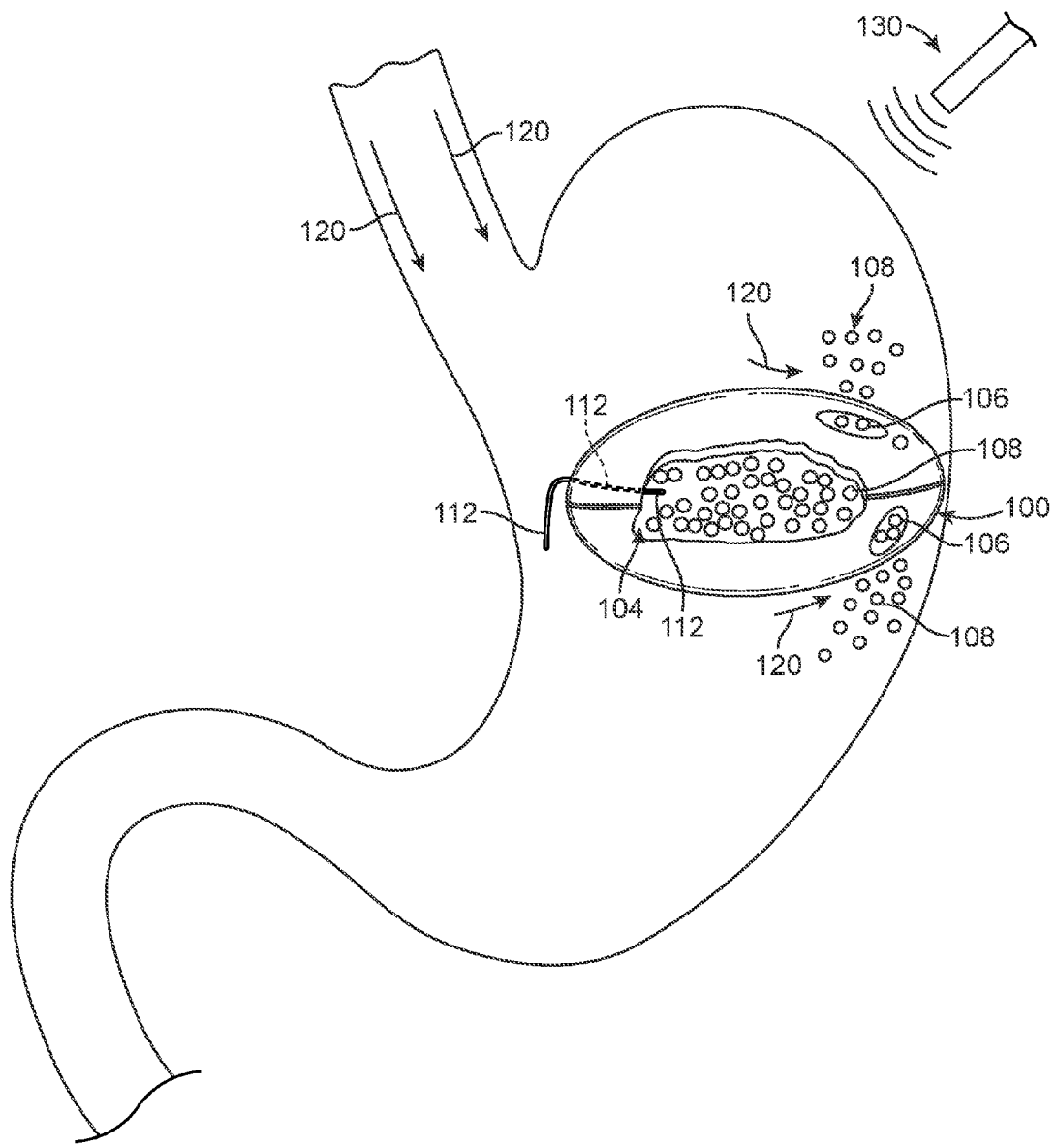
FIG. 1F illustrates a state of a device assembly after a physician, patient, or other caregiver desires to initiate release the device assembly from the body.

FIG. 1E shows the device assembly 100 after it is inflated, expanded, or otherwise transitioned to achieve a desired active profile. A physician can monitor the profile of the device assembly 100 either using a scope positioned within the stomach (not shown) or non-invasive imaging such as ultrasound or a radiographic imaging. Alternatively, or in combination, the active profile can be achieved after a pre-determined volume of fluid, liquid and/or gas is delivered to the reservoir 104. Furthermore, variations of the device can include one or more markers (such as radiopaque markers) 116 allowing a physician to determine orientation and/or size of the device assembly 100.

As noted above, this particular variation of the assembly 100 includes a conduit 114 that is coupled to the skin 102 through the fluid path 112 and extends into the reservoir 104. Alternatively, a conduit 114 can be directly coupled to the skin. When the device assembly 100 achieves the active state the conduit 114 can be pulled from the device assembly 100. For those variations that employ a sealable fluid path 112, withdrawal of the conduit 114 causes the sealable fluid path 112 to collapse or be compressed thereby preventing the contents of the reservoir 104 from escaping from the device assembly 100. Alternatively, or in combination, the sealable fluid path 112 located within the reservoir 104 can be sealed due to the increased pressure within the reservoir. In other words, the same pressure within the reservoir 104 that causes expansion of the device 100 also causes the sealable fluid path 112 to close, compress or otherwise reduce in diameter to a sufficient degree that material is unable to escape from the reservoir through the sealable fluid path 112.

In certain variations, the conduit 114 is held in place in the sealable fluid path 112 by friction alone. Withdrawal of conduit occurs by pulling on the conduit in a direction away from the device 100. During the initial stages of this withdrawal activity the expanded device 100 generally moves upwardly with the conduit in the stomach, until the expanded device 100 reaches the esophageal sphincter. With the device assembly restrained from further upward movement by the sphincter, the conduit 114 may then be withdrawn from the fluid path and from the patient by additional pulling force.

Upon withdrawal of conduit 114 the fluid path effectively seals, as described herein, and prevents migration of fluids or other substances into and out of the reservoir. In certain variations the fluid path seals on its own after removal of a conduit or other member located therein. In additional variations, hydrostatic pressure and/or pressure caused by the expanded filler acting along the length of the fluid path can aid in sealing of the fluid path.

FIG. 1F illustrates a state of the device assembly 100 after a physician or the patient desires to initiate release the device assembly 100 from the body. As discussed above, an exogenous material 120 is delivered into the stomach (or other portion of the body as applicable). As the exogenous material 120 (or exogenously activated body fluids) engage the release material 106, the release material reacts to the conditions created by the exogenous material and begins to degrade, melt, break down, or otherwise become unstable such that the physical barrier of the skin 102 becomes compromised. As noted above, additional variations of the devices can be used with an exogenous stimulus in place of or in addition to an exogenous material. For example, the exogenous substance can directly act upon the release material such as providing a substance at an elevated temperature and/or PH level that causes disruption of the release material to allow the filler material to interact with the fluids in the stomach and/or to pass from reservoir into the stomach. Alternatively, the exogenous material can interact with fluids within the body to directly or indirectly activate and/or degrade the release material.

In alternate variations, the release material, or additional areas on the skin degrade or become unstable due to the passage of time in the normal gastric environment. In such cases, the additional areas can serve as a safety mechanism to ensure release of the device after a pre-determined period of time. For example, in the variation shown in FIG. 1F, one of the areas of release material 106 can be responsive to exogenous stimulus or exogenous materials while the other release material 106 can break down over time. Alternatively, or in combination, as shown in FIG. 1F an exogenous stimuli can be used in combination with the exogenous material 120 to cause disruption of the release material. In another variation, the exogenous stimuli 130 can be used to act directly on the release material 106 (without any exogenous material) to cause disruption of the release material 106 and to begin the process of releasing the device assembly 100 from the patient.

FIG. 1F illustrates the filler material 108 escaping from the reservoir 104 as the device assembly 100 decreases from its active profile to allow for passage of the skin 102 and filler material 108 from the body. In certain variations, the consistency of the escaping filler material 108 is similar to or closely approximates the consistency of a food bolus. The matching of the consistency of the filler material to naturally occurring particles that travels within the body ease the passage of the filler material 108 through the remainder of the digestive tract. In certain situations, the instability or degradation of the release material 106 allows bodily fluids to mix with the content of the reservoir 104, which liquefies the filler material and expedites reduction of the device assembly 100 from an active profile or state. Although not illustrated, as the device assembly reduces in profile, the peristaltic movement of the muscles in the digestive tract works to extrude materials out of the device 100, allowing for the passage of the skin 102 of the device 100 through the digestive tract until it is ultimately excreted from the body. Certain variations of the device assembly can be made to have a soft, lubricious and/or malleable configuration to aid in passing through the gastrointestinal tract.

FIGS. 1A to 1F are intended to illustrate variations of devices and methods for occupying space within a patient's body, especially those devices for use within a gastric space. However, the principles described above can be used with any number of variations of the device as described below. As noted herein, combinations of different variations of devices, as well as the combinations of aspects of such variations are considered to be within the scope of this disclosure where such combinations do not contradict one another.

Figure 2:
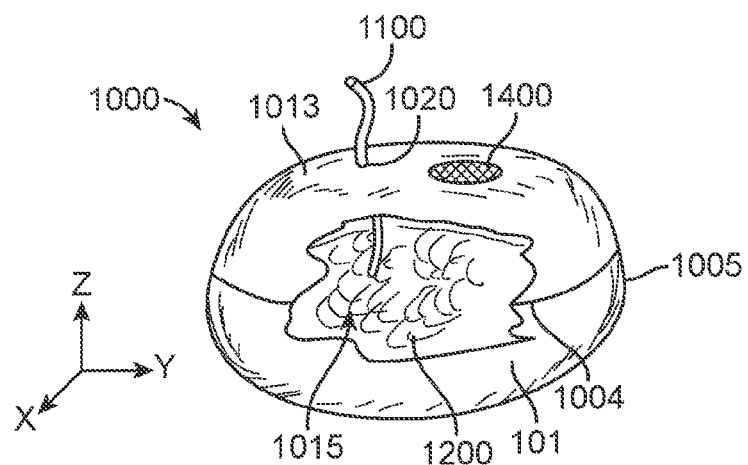
FIG. 2 shows a device assembly or construct in a hydrated or active profile whose outer "skin" defines a material reservoir or pocket.

In the embodiment shown in FIG. 2 the construct 1000 is in a hydrated or active profile and comprises a generally oblate spherical shaped structure whose outer "skin" defines a material reservoir or pocket 1010. The reservoir 1010 is bounded by a thin, flexible material surface or skin 1013 that encloses an interior volume 1015 for retaining substances that maintain the construct in the active profile. In one such variation, the reservoir 1010 contains a filler material 1200, which may be a liquid or a semi-solid or gel-like material. In general, the volume of filler material 1200 is initially low, that is, when construct 1000 is in its initial, pre-deployment condition. The volume of filler material 1200 increases after the construct's deployment. Construct 1000 in FIG. 2 illustrates the fully expanded or active state but for clarity only a representative portion of filler material 1200 is shown.

The transition from initial, unexpanded state construct 1000 to the active state can be effected by increasing the volume of filler material 1200 enclosed in reservoir 1010. Additionally, the volume can be expanded through expansion and/or swelling of the filler material already inside the reservoir 1010. For example, as was described in commonly assigned U.S. patent application publication number US2011/0295299, one exemplary embodiment filler material 1200 in the initial state is a pre-determined volume of dry hydrogel granules. The dry hydrogel granules can swell, for example, between 10 and 400 times their dry volume when exposed to an appropriate liquid, generally an aqueous solution.

In the variation shown in FIG. 2, once a medical practitioner or user deploys of the construct 1000 into the stomach, the aqueous liquid in the stomach migrates into the reservoir 1010 and creates a slurry of liquid and substantially fully hydrated hydrogel. As is well known, hydrogels absorb water from their surroundings causing swelling of the hydrogel. In the embodiment of FIG. 2, the volume of dry hydrogel is pre-selected to have a fully swollen, unconstrained volume that slightly exceeds the volume of the reservoir 1010. Under constraint, hydrogels cannot swell to a greater volume than the limits of the constraining volume; however, constrained hydrogels can and do exert pressure against the constraint. Thus, reservoir 1010 becomes a structurally self-supporting structure, when filled with an excess of swollen hydrogel (that is, when the unconstrained volume of the swollen hydrogel is greater than enclosed interior volume 1015). In other embodiments, reservoir 1010 is filled and pressurized with other filler. In its expanded state, reservoir 1010 can be sufficiently elastic to deform under external pressure and returns to its pre-deformation shape when the pressure is removed. In yet additional variations, the filler material can be selected such that it hardens after a period of time to become its own skeletal structure or to support the skin. Such a filler can be selected to eventually degrade based on the environment in the stomach or digestive tract.

Assemblies 1000 under the present disclosure can comprise a material surface or skin 1013 that is substantially impermeable to liquids and/or gases. In these embodiments, filler material 1200 can be, respectively, a liquid or a gas. Additionally, filler material 1200 can be a fluid-swellable material such as hydrogel, which, when hydrated, becomes a solid, semisolid or fluid-like gel or slurry. As illustrated in FIG. 2, embodiments comprising a substantially impermeable skin 1010 further comprise a fluid transport member 1100 that allows for the migration of fluid through the skin.

In some examples, as noted above, the fluid transport member includes a sealable fluid path that may or may not be coupled to an additional fluid conduit. In additional variations, the fluid transport member can include a localized liquid transfer member 1100 that is disposed in an orifice 1020 through the skin 1013 and facilitates the migration of fluid between the interior and exterior of reservoir 1010. One such example can be found in U.S. Provisional application entitled "Resorbable Degradation System" Ser. No. 61/723,794 filed on Nov. 8, 2012, the entirety of which is incorporated by reference herein As noted above, in certain variations, where the device assembly 1000 comprises a substantially fluid impermeable material surface, a construct 1000 in the expanded active profile can remain in stomach or other portion of the body indefinitely until released. Therefore, as noted above, devices of the present disclosure can include a release material 1400, which allow the construct 1000 to reduce in size from the active profile and ultimately pass through the body. Such an active release material 1400 configuration allows for on-demand release of the construct. As noted above, once activated, degraded, or otherwise made unstable, the release material allows migration of filler material from the reservoir and device assembly. In some variations, activation of the release material opens a passage in the skin 1013 of the device 1000. Alternatively, or in combination, activation of the release material can result in reduction of the integrity of the skin forming the barrier about the reservoir. Once the barrier is compromised, the filler material can safely pass into the body. Regardless of the means, the activation of the release material and release of the filler material collapses the device 1000 leading to egress or removal of the device 1000 through the body (in this variation through the lower gastro-intestinal track). As noted above, variations of the devices described herein include a release material that is activated by exposure to an exogenous substance.

In certain variations, the device assembly 1000, in the active profile, comprises a highly oblate spheroid wherein the skin 1013 can be a thin, film-like material that is soft, tear-resistant, flexible, substantially inelastic, and non-self adhesive. Such features can be beneficial for a device that is to be compressed into a small oral dosage form for administration. In certain examples, the skin 1013 comprised a 0.0015 inch thick polyether polyurethane film. In a simple variation, an oblate spheroid can be created from skins forming an upper material surface and a lower material surface, wherein upper material surface and lower material surface are sealed to each other as shown by seam 1004 in FIG. 2. One such means for sealing the device 1000 comprises an ultrasonic weld around the periphery of adjoining materials. As will be described in more detail below, in a possible assembly method, the upper and lower material surfaces are formed as nominally identical, substantially disk-like shapes of material, welded in a band around most of their circumferences, the assembly is then inverted (turned inside out) through an unwelded section. Once the assembly is inverted, the welded material forms the seam 1004 that projects.

Figure 3A:
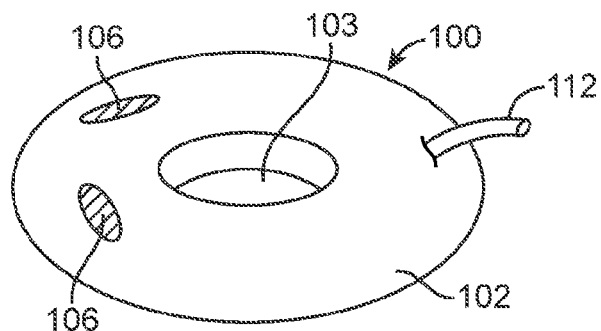
FIGS. 3A to 3E illustrate additional variations of device assemblies 100 having various active profiles.
Figure 3B:
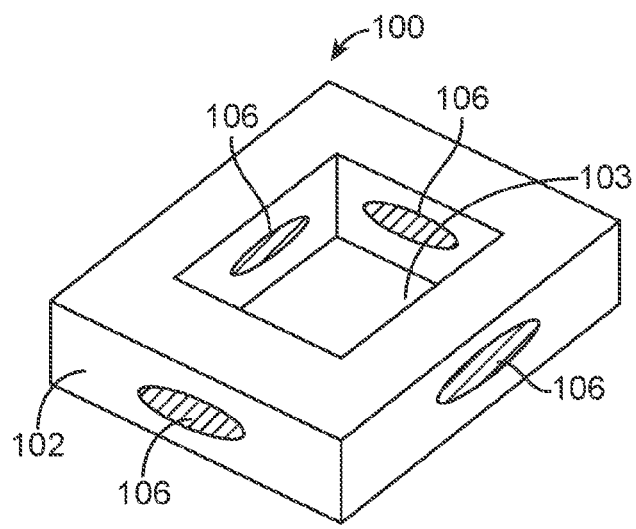

FIGS. 3A to 3E illustrate additional variations of device assemblies 100 having various active profiles. It is understood that the shapes shown in the illustrations disclosed herein are examples of possible variations of the device. FIG. 3A illustrates a device 100 having a donut shape (i.e., an oblate shape with an opening 103 in or near a center of the device assembly 100). FIG. 3B illustrates a device assembly 100 having a rectangular or square-like shape.

Figure 3C:
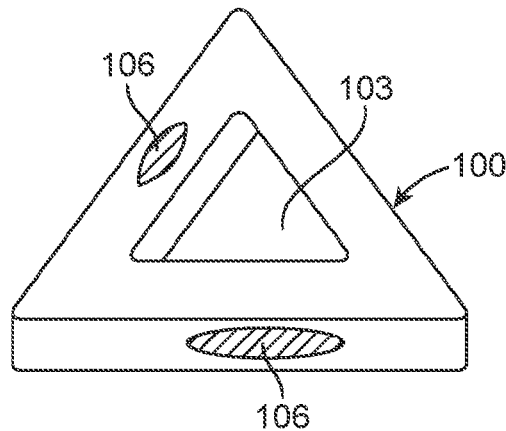
Figure 3D:
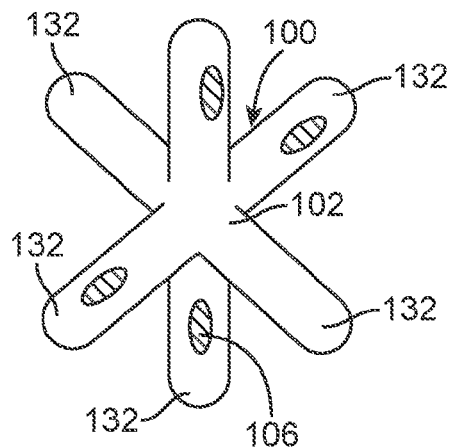
Figure 3E:
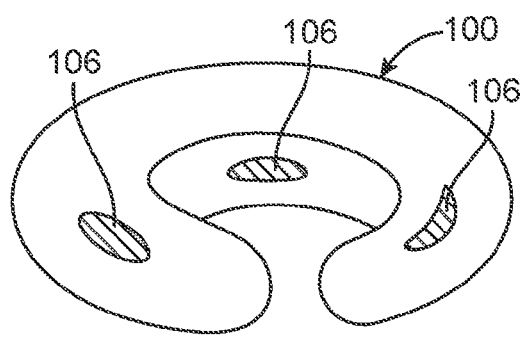

FIG. 3C illustrates a triangular shaped device assembly 100. Again, the illustrated variation includes an optional opening 103. Some variations can have a contiguous surface, while others can incorporate one or more openings 103 as shown. FIG. 3D illustrates a device assembly 100 having a shape that comprises a plurality of protrusions 132 that form the device assembly 100. The number and direction of the protrusions can vary from that shown. FIG. 3E shows a variation of a device assembly 100 having a crescent shape.

The devices shown in FIGS. 3A to 3E also show release materials 106, whether located on an interior of an opening 103 or on an exterior of the shape. The variations shown in FIG. 3A to 3E can also include the additional features of the device assemblies described herein.

Alternatively, the release material can comprise a filament, clip, band, cap, or other structure that mechanically closes the edges of the skin. Further, as described below, a source of stored energy, such as a loaded spring or compressed sponge or other material, may be included in the release assembly, where such kinetic energy is also released upon activation of the release material and which may improve the performance of such assembly.

Figure 4:
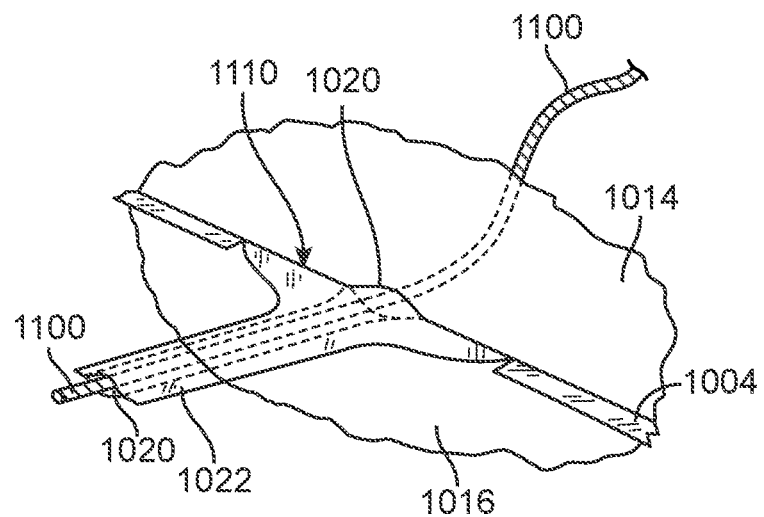
FIG. 4 illustrates a variation of a fluid transfer member also having a sealable fluid path for use with the device assemblies described herein.

FIG. 4 illustrates a variation of a fluid transfer member 1100 also having a sealable fluid path 1110 for use with the device assemblies described herein. In this example the fluid transfer member 1100 also includes an elongate fluid conduit, or tube, that passes through a tunnel valve that functions as a sealable fluid path 1110. The tunnel valve 1110 can be positioned in an orifice in the upper 1014 or lower 1016 material surfaces or in an opening in a seam 1004 of the device assembly. This variation of the tunnel valve 1110 comprises an elongate portion 1022 that extends within the reservoir of the device assembly. In some variations, the tunnel valve can extend beyond the seam 1004 or beyond the exterior surface of the device assembly as discussed above.

As illustrated in FIG. 4, portion of the fluid transport member includes a tunnel valve 1110 that can comprise two layers forming an orifice 1020. The orifice 1020 forms a fluid path that allows a remainder of the fluid transport member 1100 to deliver fluids into the reservoir. In this variation the fluid transport member 1100 further comprises a conduit. However, as noted herein, the fluid transport member can comprise a wick type device or any fluid source that allows delivery of fluids into the reservoir of the device. As also noted herein, a variation of the device permits a portion of the fluid transport member 1100 to be detachable from the tunnel valve 1110 where detachment permits the tunnel valve 1110 to prevent egress of fluids or other substances from within the reservoir. Sealing of the tunnel valve 1110 can occur via a rise in pressure within the reservoir. Alternatively, or in combination, a number of other mechanisms can result in sealing or closure of the orifice 1020 in the tunnel valve 1110. For example, in additional variations the surfaces forming the orifice 1020 can seal upon contact or the length of the tunnel valve 1110 combined with its flexible nature can simply make it difficult for substances, such as an expanded hydrogel, to travel through the elongated portion 1022 of the tunnel valve.

FIG. 4 also shows the conduit 1100 extending through the tunnel valve 1110 such that it extends into the reservoir. However, in alternate variations, the device end of conduit 1100 can remain within an interior of the orifice 1020 of the tunnel valve 1110.

Figure 5:
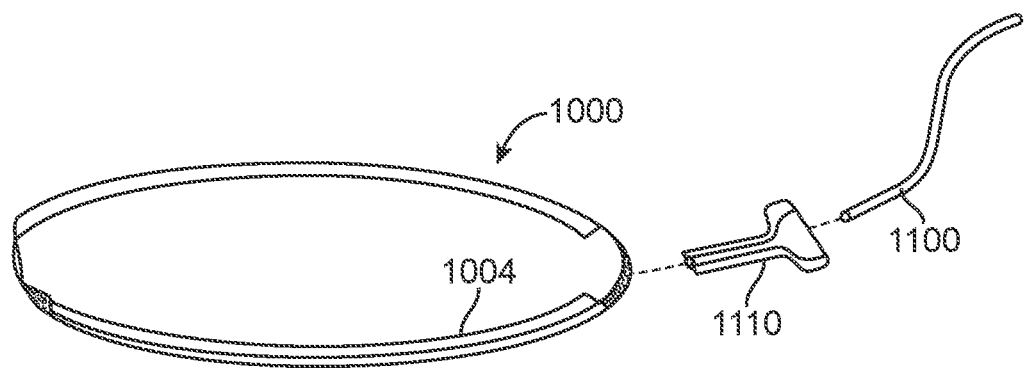
FIG. 5 shows a variation of a tunnel valve.

In one variation of the tunnel valve 1110, as illustrated in FIG. 5, the tunnel valve 1110 shaped roughly as the capital letter T, wherein the vertical stem of the T comprises the elongate passage 1022 and wherein the crossbar of the T, in part, forms an increased attachment surface that can be attached to the skin as noted above. As may be seen in FIG. 5, tunnel valve 1110 can be disposed through an opening in the seam 1004.

Some examples of materials used to form a tunnel valve include thin, film-like materials. For example, variations include tunnel valve materials that have properties similar to the material used in material surface or skin of the device. Additional materials include but are not limited to polyurethane, nylon-12, and polyethylene. Such layers can be between 0.001" and 0.1" thick. In one example a tunnel valve included a thickness of 0.0015"

Figure 6A:
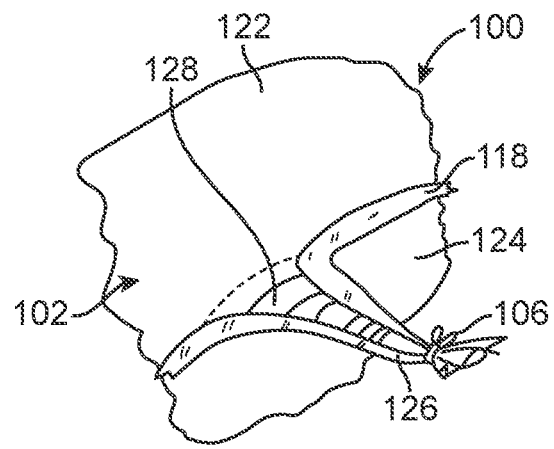
FIG. 6A illustrates a partial view of a variation of an invaginated section of a skin of a device assembly.

As discussed above, variations of a device assembly include a release material that is coupled to a portion of the skin to form a barrier to retain substances within a reservoir of the device. FIG. 6A illustrates a partial view of a variation of an invaginated section 126 of a skin 102 of a device assembly 100. As discussed herein, the skin 102 can include an first surface 122 and second surface 124 joined at a seam 118. The seam 118 can include any number of unjoined sections that are intended to function as release areas 128. In the illustrated example, the release area 128 is bounded by an invaginated section 126 of the skin 102. The invaginated section 126 of the skin can comprise a tuck, fold, pucker, bulge, extension, etc. in the skin 102. Alternatively or in addition, the invaginated section 126 can be formed within a first 122 or second 124 surface of the skin 102 rather than within a seam 118.

The release area 128 of the invaginated section 126 ordinarily forms a passage that is fluidly sealed by a release material 106. The release material can comprise a mechanical closure (such as a staple-type structure or a filament that ties together the invaginated structure). Alternatively, or in combination, the release material 106 can comprise a temporary seal or other joining of the edges of the invaginated section 126. In additional variations, the release material can extend outwardly from an exterior surface of the skin. In some variations, the release material 106 is disposed on the invaginated portion 126 sufficiently close to the skin to be affected by a temperature increase caused by delivery of the exogenous substance.

Figure 6B:
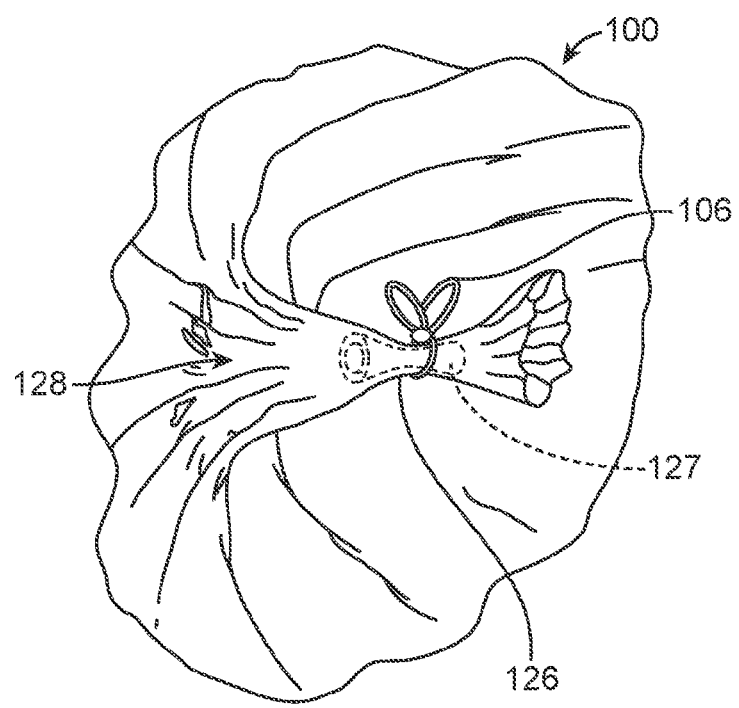
FIGS. 6B and 6C illustrates a partial view of the interior of a device assembly comprising an invaginated section of the skin further having energy storage element that assists in opening of the device in response to an exogenous trigger.

Other variations of a device assembly 100 include an energy storage element that encourages a rapid and more complete opening of the release area 128. FIG. 6B illustrates a partial view of the interior of a device assembly 100 comprising an invaginated section 126 of the skin 102. As was discussed in relation to the variation of FIG. 6A, the release material 106 in this variation forms a temporary seal by tying off the invaginated section 126. In this variation, an energy storage element 127 is disposed within the invaginated section 126 of the release area 128 and is further disposed to be within the region tied off with the release material 106.

Energy storage element 127 is, generally, a compressible elastic material, for example a latex foam. In some variations energy storage element 127 is generally cylindrical with a diameter at least fractionally smaller than the diameter of the invaginated section 126. As shown in FIG. 6A, when device 100 is deployed in the body, release material 106 is tied firmly around the invaginated section 126 at the position of the energy storage element, thereby simultaneously sealing the invagination and compressing the energy storage element. This compression of the elastic material in the energy storage element 127 generates a tension in the release material tied around the invaginated section 126 that is greater than the tension in the release material tie used to seal an invagination alone.

Figure 6C:
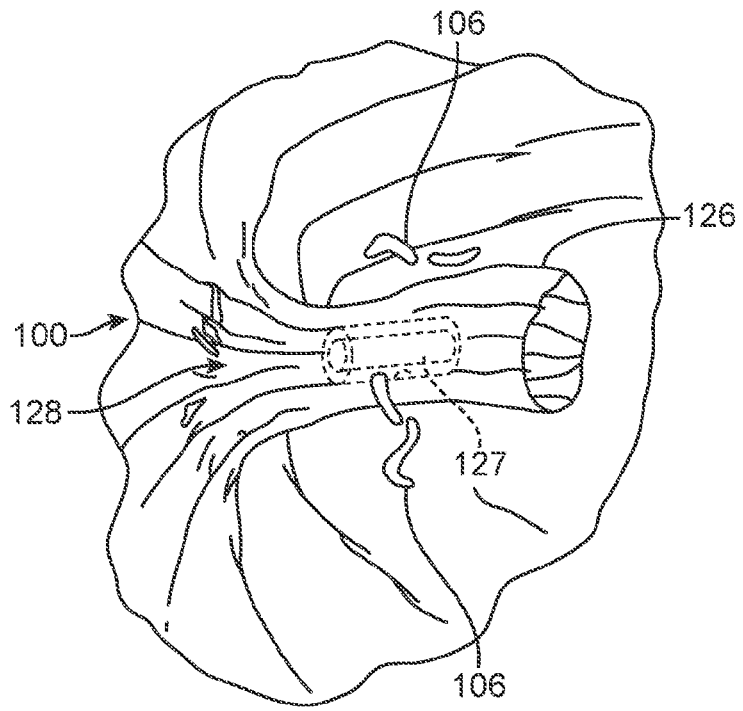

FIG. 6C illustrates the invagination section 126 after an exogenous trigger has been used to activate the release material 106. As illustrated in the figure, the release material is broken apart in several small segments, allowing the invaginated section 126 to open and release the filler material, not illustrated for clarity. The increased tension generated by the energy storage element encourages the release material to break apart sooner, more rapidly and more completely than it otherwise would.

Examples of the release material can include poly(caprolactone) or PCL. In such variations, PCL softens, melts, and weakens above a pre-determined temperature. In some cases the pre-determined temperature is greater than normal body temperature. Accordingly, in such variations, the exogenous substance can comprise a heated fluid that can raise the temperature of the PCL without causing injury to the adjacent areas of the body. As the PCL release material degrades, the structural integrity of the joined region of the release section (such as the invaginated section 126) decreases. In one example, the release material is a modified PCL, wherein the modification comprises lowering the melting point of unmodified PCL from its normal melting temperature to a human-tolerable temperature.

For example, an on-demand degrading construct composed of nylon-12 can be constructed by first fabricating a 1" circular annulus of 1.5 mil Pollethane, also known as 55DE Lubrizol 2363 polyether polyurethane (available from Specialty Extrusions Inc. of Royersford, Pa., USA). A circular degradable patch of poly(caprolactone) (PCL) (with a melting point, $T_m$, equal to ~47° C.; available from Zeus Industrial Products of Charleston, S.C., USA) can be RF-welded to the Pellethane annulus, covering the hole, creating a $T_m$-modified PCL patch surrounded by a rim of Pollethane. The Pollethane rim can then be RF-welded to a sheet of nylon-12, which can then be used for further construction.

Examples of release materials can include biocompatible manufactured polymers. Table 1 is a compilation of some pertinent properties of several biocompatible materials that can be extruded or otherwise manufactured in filamentary form and which also can be degraded. Some of these materials, poly(vinyl alcohol) are stable in dry environments but dissolve very quickly in moist environments. Other materials either dissolve quickly in caustic solutions (e.g. extremely alkaline) or melt quickly at high temperatures, but these conditions all exceed those that can be tolerated by humans. Some biocompatible polymers, for example co-polymers of methacrylic acid and methyl-methacrylate, dissolve in liquids having physiologically relevant pHs. For example, they remain stable at pH<7.0 but dissolve at pH>7.0.

| Polymer | Type | Degradation Mode | Degradation Condition | Degradation Time |
|---|---|---|---|---|
| Poly(glycolic acid) | Bioabsorbable | Gradual hydrolysis | Exposure to water or acid | 2-3 months |
| Poly(dioxanone) | Bioabsorbable | Gradual hydrolysis | Exposure to water or acid | 6-8 months |
| Poly(lactic-co-glycolic acid) | Bioabsorbable | Gradual hydrolysis | Exposure to water or acid | 2 months |
| Poly(vinyl alcohol) | Bioabsorbable | Rapid dissolution | Exposure to any aqueous solution | Seconds |
| Methyacrylic acid methyl-methacrylate co-polymers | Bioabsorbable | Hydrolysis; on-demand pH-dependent dissolution | Exposure to alkaline pH | Days at near neutral pH and minutes to hours at alkaline pH |
| Poly(caprolactone) | Bioabsorbable | Hydrolysis; on-demand at temperatures greater than 60° C. | Exposure to heat | 6 months at temperatures less than melting point, seconds at or above melting point |
| Polyester | Non-bioabsorbable | None | None | N/A |
| Poly(propylene) | Non-bioabsorbable | None | None | N/A |
| Nylon | Non-bioabsorbable | None | None | N/A |

As the release section opens the reservoir to the surrounding environment the opening provides an open path out of the device assembly. The open path allows the contents of the device assembly, such as the filler material, to become exposed to the gastric contents and freely to exit reservoir. When positioned within the stomach, normal gastric churning assists in emptying the contents of the device assembly allowing for the entire device along with its contents to pass from the body. In some variations, the membrane that forms the skin will provide little or no structural support. This configuration allows the body's natural squeezing strength to be sufficient to extrude any reasonably viscous substance out of the device assembly.

Figure 6D:
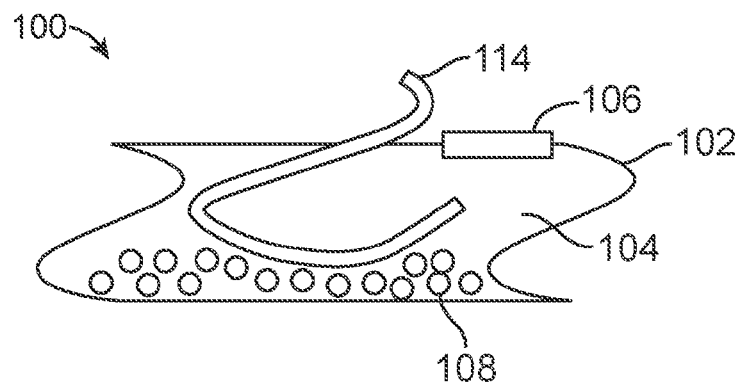
FIG. 6D provides a schematic illustration of another example of a device assembly having a release material located on a surface of the skin.

FIG. 6D provides a schematic illustration of another example of a device assembly 100 having a release material 106 located on a surface of the skin 102. One example of such a release material comprises a degradable patch 106 that, when degraded, opens the physical barrier surrounding the reservoir 104 to allow filler material 108 (swollen or unswollen) to exit the device assembly 100. The device assembly 100 comprises a skin material to which release material 106 can be joined (e.g. by heat sealing, RF-welding, impulse heating, or any other means). In certain variations, the release material/degradable patch 106 comprises a material or combination of materials that remains impermeable to water and hydrogel after deployment and can be degraded "on-demand" in response to an exogenous substance or in response to a condition created within the body being the result of the administration of the exogenous substance.

In one example, the release material can range from 25 microns thick; up to 2.5 millimeters thick. In another example, release material is a modified poly(caprolactone) with melting point $T_M=47°$ C. (available from Zeus Industrial Products of Orangeburg, S.C. USA). In additional embodiments, degradable patch 106 may be poly(glycolic acid) or poly(L-lactide acid) (available from Poly-Med, Inc of Anderson, S.C.).

Figure 7A:
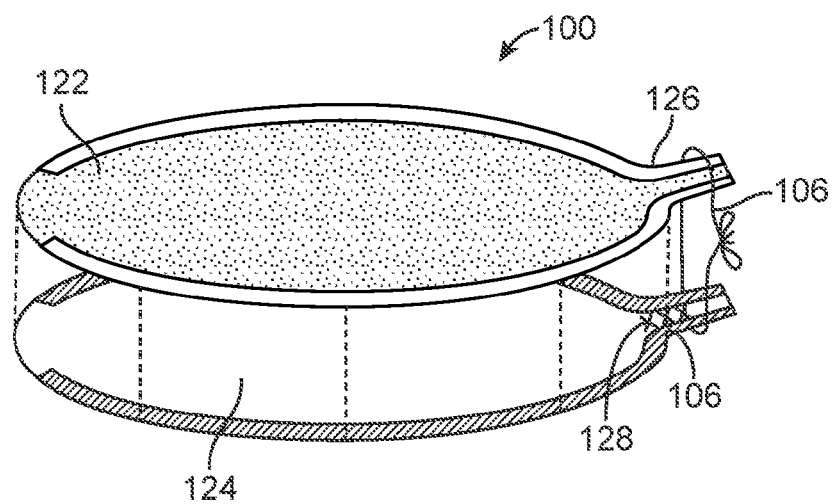
FIGS. 7A and 7B show one example of an exploded, assembly view of a device assembly.
Figure 7B:
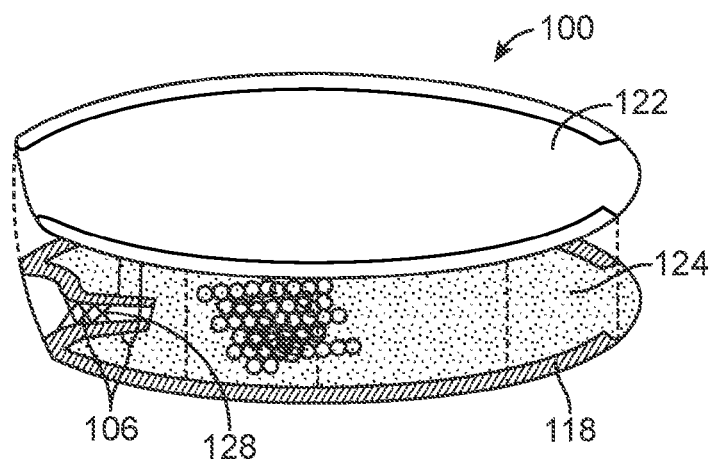

FIGS. 7A and 7B show one example of an exploded, assembly view of a device assembly 100 (where a fluid transport member is omitted for the sake of clarity). As shown, the device assembly 100 can include a material skin comprising two layers of material that form an upper skin 122 and a lower skin 124. As noted herein, the layers can be joined to form a seam. Clearly, the presence of a seam is optional and some variations of devices under the present disclosure will not include a seam or will have similar types of joined regions of material to preserve the skin as a physical boundary for the contents of the reservoir. Again, the device assembly 100 is shown in the shape that eventually assumes an oblate spheroid shape. However, other shapes are within the scope of this disclosure. In one variation, the skin comprises substantially inelastic materials 122 and 124 that are joined around a perimeter leaving openings as discussed herein. It will be understood that, the shape of the device referred to as an oblate spheroid for descriptive purposes. In other embodiments wherein one or more devices may be joined to comprise a multi-bodied assembly, each individual device can be assembled from one or more sheets of film-like material that are cut to a pre-designed shape. FIG. 7A shows the device 100 in an inside-out configuration in mid-assembly. As shown, the invaginated portion 126 can be secured with a filament release material 106 and/or a sealing release material 106 located within a release area 128. FIG. 7B illustrates an exploded view of the construct of FIG. 7A after the structure is inverted and a filler material is inserted into a reservoir formed by the skin materials 122 and 124.

Material Surface or Skin

The type of material or skin will depend upon the intended application. In some variations, a skin will be chosen as a balance of selecting a sufficiently thick film-like material that has adequate strength. For example in some variations, tear resistance can be preferred to enable the finished construct to be compression into as low a volume capsule as possible. The inventors have determined that thin films with a thickness ranging from 0.5 mils to 4 mils are generally suitable. However, the devices described herein can comprise a greater range of thicknesses depending upon the particular application, including a range of thicknesses in different parts of the same construct. In some embodiments, the film-like material must be weldable or adherable to other materials such as might be used in valves 1110, filler material release mechanisms 1400, and/or attachment interfaces as described herein.

In additional embodiments, the film-like material exhibits low transmission rate of filler material, both before and after device expansion. In some embodiment the film-like material exhibits a low moisture vapor transmission rate. Additionally, some film-like material also exhibits high chemical resistance to the variable conditions encountered in the stomach. These conditions include low pH, high salt, high detergent concentrations (often in the form of bile salt reflux), enzymatic activities (such as pepsin), and the variable chemistries of chyme that depend upon the nature and content of consumed food. For those devices used in the gastric space, the material must also be comprised of biocompatible materials that can safely be in contact with the gastric mucosa for the duration of the treatment course.

The devices described herein can use numerous thermoplastic elastomers, thermoplastic olefins and thermoplastic urethanes that can be extruded or cast into single-layer or multi-layer films which are suitable for embodiments of the gastric device. Example base resins that may be employed include polypropylene, high-density polyethylene, low density polyethylene, linear low density polyethylene, polyester, polyamide, polyether polyurethane, polyester polyurethane, polycarbonate polyurethane, bi-axially oriented polypropylene, Polyvinylidene chloride, ethylene vinyl alcohol copolymer, and Ethyl Vinyl acetate. Some embodiments comprise single layer films whilst other embodiments comprise multiple layer films. Other embodiments consist of multilayer films including one or more tie layers to prevent layer separation.

In some embodiments, the film-like material may be coated with other materials. For example, in some embodiments hyaluronic acid coatings can be employed to improve softness and lubriciousness. In other embodiments, coatings such as Parylene® can be applied to improve the chemical resistance of the gastric mucosa-exposed film surface. In some embodiments, wax coatings, PVDC coatings, vacuum-metallization, or Parylene® coatings may be applied to the surface of the film to reduce its moisture vapor transmission rate.

In one example, the film-like material used comprised a 1.5 mil polyether polyurethane film. In other embodiments the film-like material is a 1 mil nylon 12 film or a 1.5 mil LLDPE film. In another example, the film-like material consisted of a multi-layered structure comprising an outer layer of polyurethane, a middle layer of PVDC or EVOH, and an inner layer of polyurethane.

Filler Material

Generally, a filler material that has a high swelling capacity and achieves a semi-solid consistency is useful to enable the finished construct to be compressed into as low a volume initial state as possible but still maintain rigidity once expanded. However, unless specifically noted, variations of the device can employ a number of different types or combinations of filler materials. During various experiments, it was determined that superabsorbent hydrogel polymers with a mass:mass swelling capacity of between 100 and 1000 are generally suitable, where a mass:mass swelling capacity of 100 is defined herein to mean that 1.0 g of dry hydrogel will absorb water and swell to become a semi-solid mass of 100.0 g.

Typically, suitable hydrogels swell maximally in the presence of distilled water and a number of these hydrogels also de-swell (releases bound water) in the presence of the variable environmental parameters encountered in the stomach. For instance, parameters such as pH, salt concentration, concentrations of emulsifying agents (often in the form of bile salt reflux), enzymatic activities (such as pepsin), and the variable chime chemistries, which depend upon the nature and content of consumed food can affect the swelling/deswelling behavior of certain hydrogels. Typical hydrogel swelling times range from between 5 minutes and 1 hour. In one variation, the hydrogel fully swells in under 15 minutes and fully de-swells in less than 10 minutes after exposure in certain environments. Many hydrogels are supplied with particle sizes distributed between 1 and 850 microns. In certain variations, gastric applications benefit from the use of hydrogel particle sizes distributed between 1 and 100 microns. In addition, the hydrogel must also be comprised of biocompatible materials that can be safely in contact with and excreted by the gastrointestinal tract. Examples of such biocompatible superabsorbent hydrogel polymers that possess swelling capacities, swelling times, and de-swelling times suitable for embodiments of gastric construct include poly(acrylic acid), poly(acrylamide), or co-polymers of poly (acrylic acid) and poly(acrylamide). Another such material that can be used as a filler material is a crosslinked poly (acrylic acid) with particle size distribution ranging from 1-850 microns and swelling capacity of 400.

Shapes

As discussed above, certain variations of the device approximate a highly-oblate spheroid comprising a diameter in the X-Y plane and a thickness along the Z-axis as illustrated in FIG. 2. In certain variations, the expanded dimensions of the device assembly can range from having a diameter between 2 inches and 10 inches. In another embodiment, the diameter of the construct is approximately 4.6 inches. The Z-axis thickness can range between 2 inches and 5 inches. However, the device assembly, unless otherwise claimed, is not limited to any particular dimension. The data below of construct parameters provides the experimentally determined dimensions of two constructs having the oblate spheroidal shape.

| Parameter | Construct 1 | Construct 2 |
| --- | --- | --- |
| Unexpanded diameter (inches) | 4.7 | 5.8' |
| Maximum swollen volume | 300 ml | 500 ml |
| Expanded diameter (inches) | 3.64 | 4.63 |
| Expanded thickness (inches) | 2.40 | 2.46 |

Liquid Transfer Valves

Figure 8A:
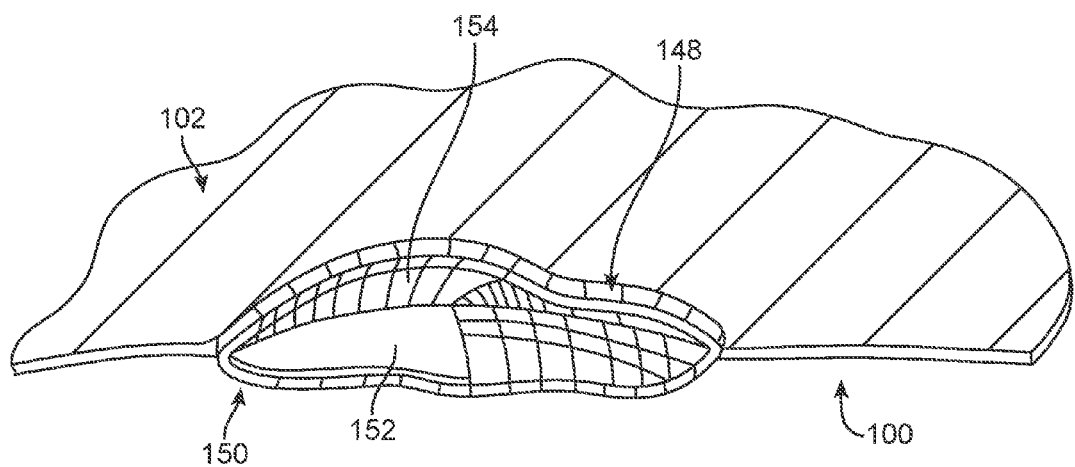
FIGS. 8A and 8B show an additional variation of a portion of a device assembly that provides a control over the fluid permeable path through otherwise impermeable material surface.
Figure 8B:
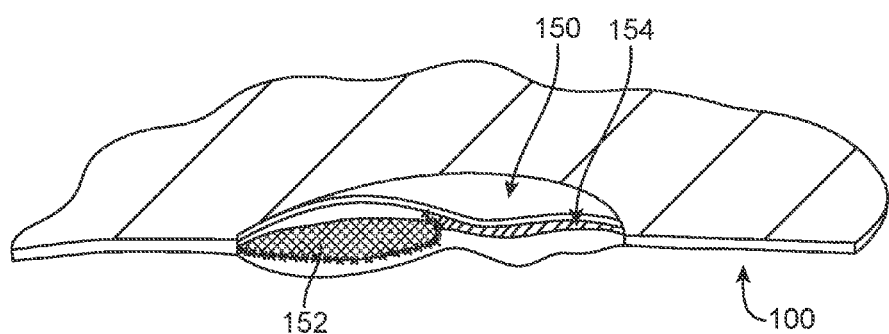

FIG. 8A shows an additional variation of a portion of a device assembly, in other embodiments liquid transfer member comprises a valve 150, wherein valve 150 is disposed in orifice 148 and provides a control over the fluid permeable path through otherwise impermeable material surface 102. In some embodiments valve 150 comprises a multilayer material structure composed of regions of permeability 152 juxtaposed against regions of impermeability 154, whereby fluid may transmigrate between the exterior and the interior of reservoir when the regions of permeability 152 and impermeability 154 are not pressed together in tight juxtaposition and whereby fluid is inhibited from transmigrating when the regions 152, 154 are pressed together tightly. In some embodiments valve 150 is self-closing. That is, valve 150 changes from allowing fluid transmigration to inhibiting fluid transmigration without external activation. In one embodiment valve 150 self-closes in response to the increasing pressure of the expanding filler material or increasing pressure within the reservoir, for example, swelling hydrogel pressing the regions 152, 154 sufficiently close together to form a barrier.

As noted above, the device assemblies described herein can include a wick-type structure that serves as a source to deliver fluids into the reservoir. One example of such a wick includes a filamentary material capable of conducting a liquid from one end to the other by capillary action. The wick can be used in a stand-alone manner or with a self closing valve.

In yet other embodiments liquid transfer mechanism 1100 comprises a mechanical valve. Mechanical valves of suitably small dimensions, comprising biocompatible materials, are well known in the art and are commercially available. A mechanical valve that serves as liquid transfer mechanism 1100 comprises a one-way or "check" valve design which allows fluid to enter reservoir 1010 but prevents fluid from exiting the reservoir. Alternatively, a mechanical valve that serves as liquid transfer mechanism 1100 may have a normally open state but which self-closes when internal fluid pressure is greater than external fluid pressure.

Figure 9A:
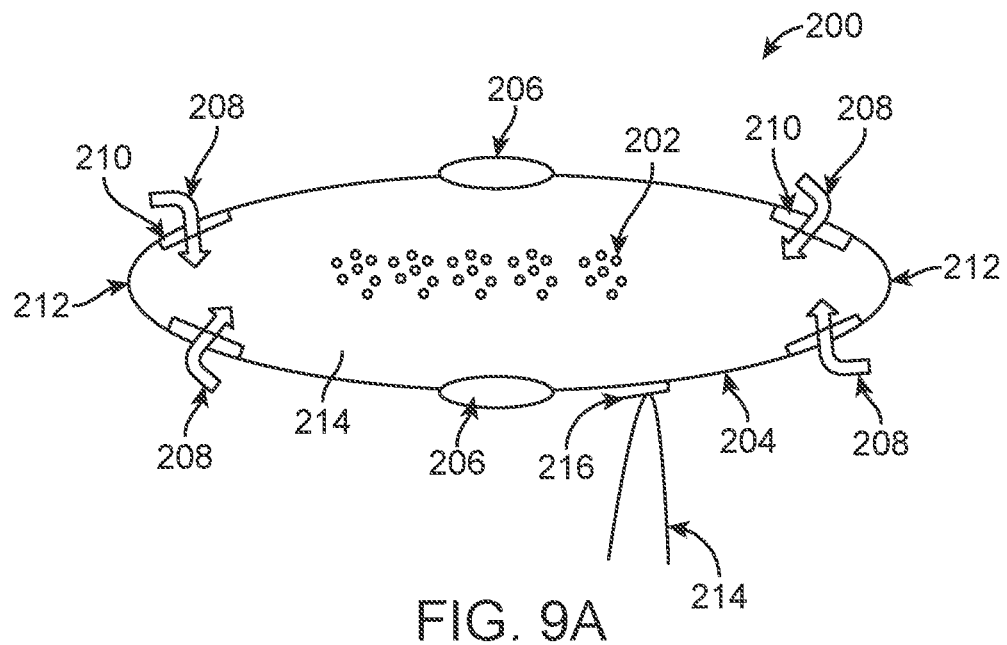
FIG. 9A shows another aspect of devices as described herein comprising one or more fluid transport members.
Figure 9B:
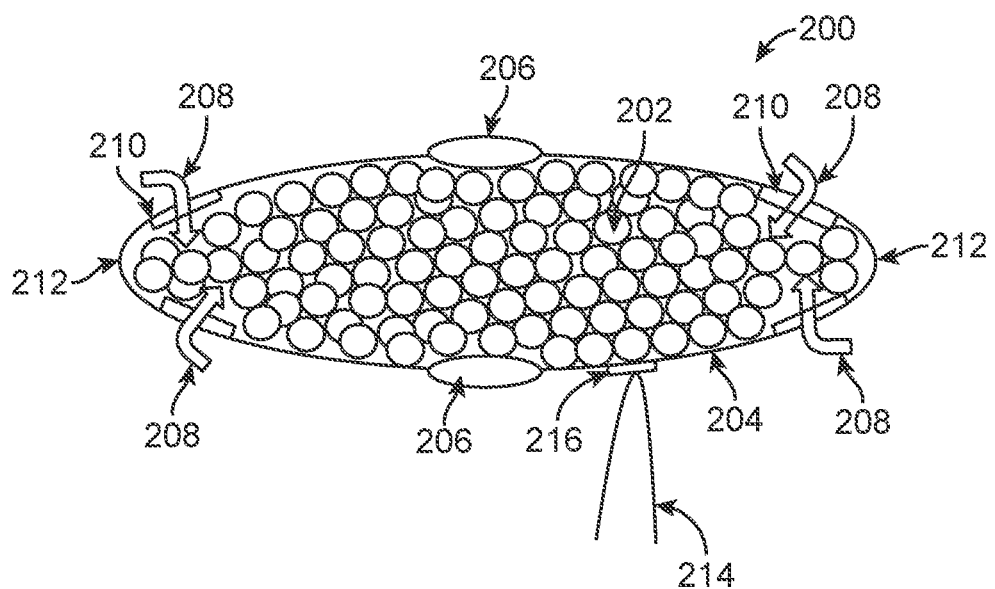
FIG. 9B also illustrate a device having a delivery system attached thereto.

FIG. 9A shows another aspect of devices as described herein, for example, construct 200 can comprise one or more fluid transport members 208. As discussed herein, the liquid supply sources 208 are configured to allow fluid to enter the reservoir to combine with a filler material 202 disposed in an unexpanded device assembly 200. In some variations, the fluid transport member 208 can be coupled to a valve 210 that reduces, blocks or stops transport of liquid when filler material 202 is substantially hydrated as shown in FIG. 9B. Such a shut off ability is beneficial as it reduces the likelihood of filler material 202 becoming contaminated by gastric contents when the device assembly is in the active profile. Examples of such shutoff-mechanisms are described herein. FIGS. 9A and 9B also illustrate variations of the device assemblies 200 as including a tether 214 or other delivery system coupled to an attachment interface 216. FIG. 9A also illustrates two areas on the skin of the device having sections of release materials 206. As noted herein, the release material is responsive to an exogenous substance that causes degradation, melting, and/or other instability of the release material to allow exposure of the reservoir to the body. This allows the contents of the reservoir to pass from the device and eventually allows for the device to pass from the body.

FIGS. 9A and 9B also illustrate a device 200 having a delivery system 214, 216 attached thereto. The delivery system 214, 216 can comprise a filamentary tether 214 that is, generally, attached to the body of the device 200 via an interface 216. The attachment interface 216 can be designed as a structurally inherent part of the delivery system (i.e., it cannot be removed from the device body as a separate, stand-alone item). Alternatively, the interface 216 can be designed as an element that is added on to device 200.

Valves

Figure 10A:
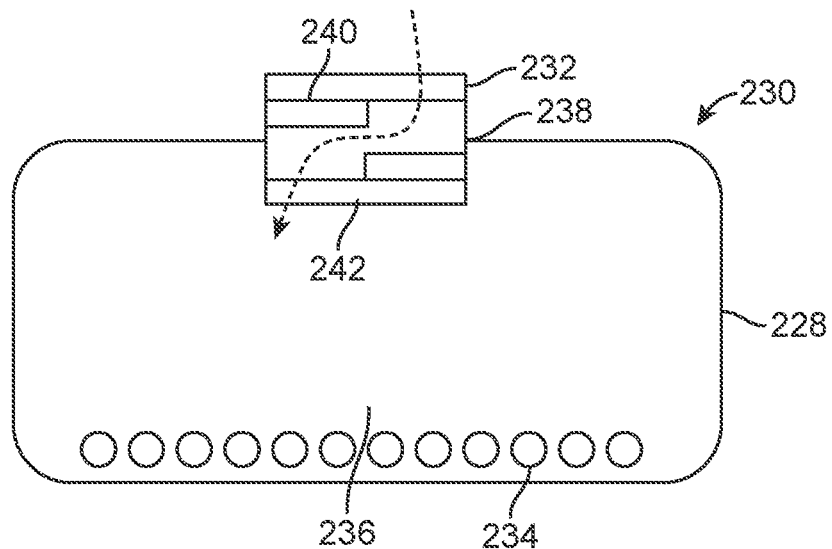
FIGS. 10A and 10B an example of a valve driven by expansion of filler material within a reservoir of the device assembly.
Figure 10B:
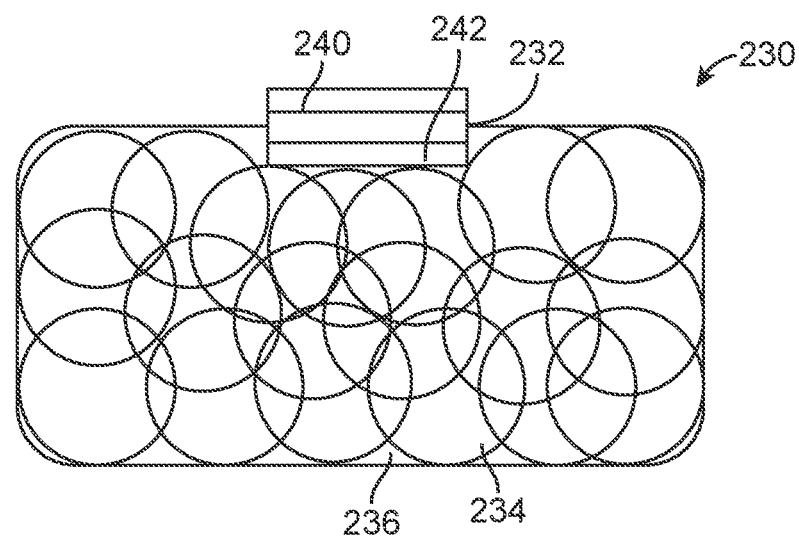

FIGS. 10A and 10B illustrate one example of a valve driven by expansion of filler material 234 within a reservoir 236 of the device assembly 230. The valve 232 is positioned or otherwise disposed in an orifice 238 in the material surface or skin 232. This permits fluid to flow into or out of the reservoir 236 when the valve 232 is in an open configuration. In some variations, the orifice 238 comprises, typically, a small percentage of the total surface area of material surface 228. Material surface 228 is generally impervious or of limited permeability to the fluids in which device 230 is typically immersed. Orifice 238 can be an opening in the otherwise fluid-tight barrier formed by the skin 232.

FIG. 10A also illustrates a pre-determined amount of filler material 234 within the reservoir 236. In some variations, the pre-determined amount is generally measured by dry mass. The dry mass of filler material 234 is determined by the amount of filler material 234 needed to fill the known volume of the expanded device 230 when the filler material is fully hydrated. When expanded, the filler material applies a pressure within the reservoir 236, which provides a shape-restoring force that resists externally applied deforming forces.

FIG. 10A also shows valve 232 covering the orifice 238. This variation of the valve 232 includes one or more flow control layers 240 that aid in closing of the valve upon action by the filler material 234. FIG. 10B illustrates expansion of the filler material 234, which increases pressure against the valve 232 and closes the fluid path by compressing the flow control layers 240

Turning back to FIG. 10A, before filler material 234 expands, valve 232 is fully open; that is, it allows fluid to pass through the valve in either an inward or outward direction. On the other hand, after filler material 234 expands, typically via hydration, the valve 232 fully closes, as shown in FIG. 10B.

In some embodiments valve 232 comprises a filler material containment layer 242. Generally, containment layer 242 is at least partly fluid permeable and simultaneously able to contain filler material 234, in its dry or its hydrated state, within construct 230. In some embodiments filler material containment layer 242 is also a flow control layer; that is, a single layer in valve 230 can simultaneously be a part of the flow control function of valve 232 and perform the filler containment function of containment layer 240.

Figure 10C:
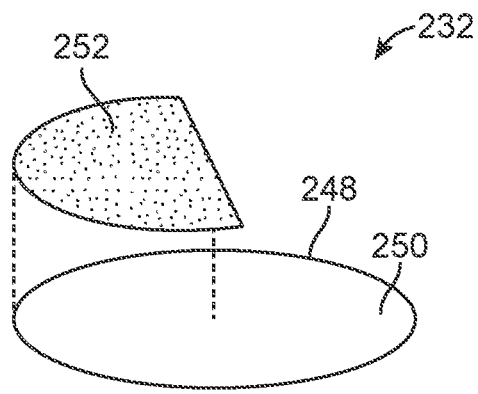
FIGS. 10C and 10D show another variation of a valve.
Figure 10C:
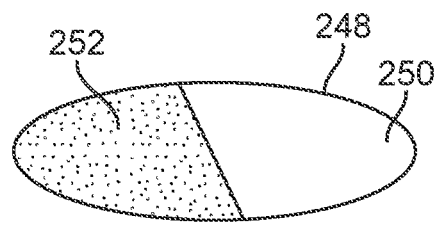
Figure 10D:
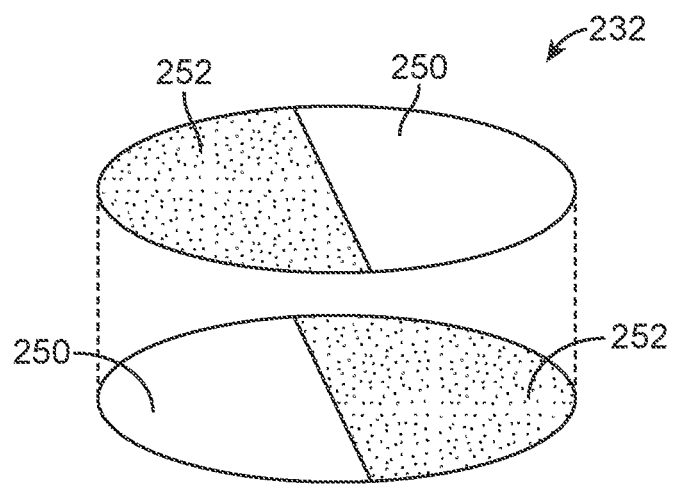

FIGS. 10C and 10D show another variation of a valve 232. In this example the valve 232 comprises more than one layer. As shown, this hybrid valve 232 comprises two demilunar flow control layers 248, each of the layers having a hybrid construction being permeable in some generally semi-circular (viz., demilunar) regions 250 and impermeable in other regions 252. The impermeable regions 252 of one layer are at least complementary to the permeable regions of the second layer; that is, where one layer has a permeable region the other layer has an impermeable region; generally there will be regions in which both layers are impermeable. Examples of the materials include a permeable patch comprising a polyester mesh and an impermeable semicircular patch comprising latex.

As illustrated in FIG. 10D, hybrid valve 232 comprises two substantially identical demilunar hybrid flow control layers, one on top of the other, wherein the two layers are oriented so that impermeable region 252 of a first hybrid control layer is aligned with the fluid permeable region 250 of a second hybrid flow control layer. By symmetry, impermeable region 252 of second hybrid flow control layer is aligned with the fluid permeable region 250 of first hybrid flow control layer. The two layers are affixed, typically with glue, around their periphery only, thereby allowing the central areas of the two layers to move apart freely.

Figure 10E:
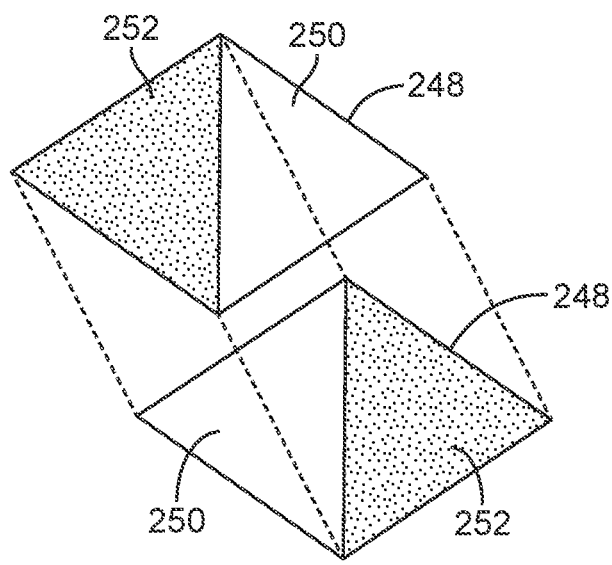
FIG. 10E shows a hybrid valve wherein each hybrid flow control layer is generally rectangular and the impermeable region and permeable region are triangular.

It will be obvious to one of ordinary skill in the art that the circular shape of exemplary hybrid valve is a design choice made primarily to simplify alignment during assembly and installation. The principle of operation of a hybrid valve— that the two flow control layers have complementary permeable and impermeable regions—is independent of the peripheral shape of the valve or the orifice to which the valve shape and size is matched. For example, another exemplary hybrid valve is illustrated in FIG. 10E wherein each hybrid flow control layer 248 is generally rectangular and the impermeable region 252 and permeable region 250 are triangular.

Figure 10F:
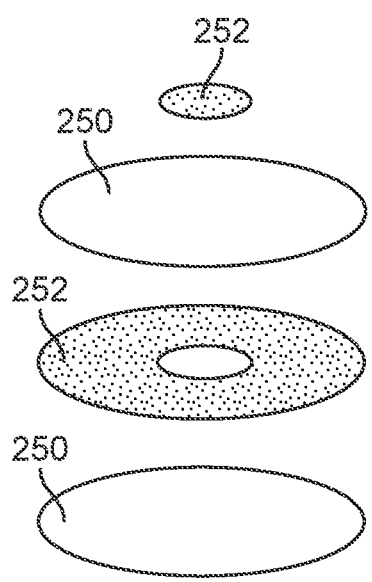
FIG. 10F shows an exploded view of a valve assembly, a permeable region in one individual flow control layer may be, for example, a circular region, and the impermeable region may be an annulus disposed around the circular permeable region.

Furthermore, permeable region 250 and impermeable region 252 in any individual flow control layer need not have identical shapes. For example, as shown in FIG. 10F, which shows an exploded view of a valve assembly, a permeable region in one individual flow control layer may be, for example, a circular region, and the impermeable region may be an annulus disposed around the circular permeable region. However the two layers of any one hybrid valve must at least have complementary permeable and impermeable regions; that is, when the two layers are overlaid there is no permeable area in communication with the exterior of the device.

In these exemplary embodiments of a hybrid valve, the flow control layer disposed on the internal side of the valve preferably can also function as filler material containment layer, with containment being achieved by the mesh comprising permeable patch. Alternatively, a separate innermost filler material containment layer must be added to the assembly.

In other embodiments, hybrid flow control layer is fabricated by joining a patch of permeable material and a patch of impermeable edge-to-edge, wherein the joint may be a butt joint, for example, or a lap joint, for a second example, wherein further the outer periphery of the edge-joined materials is designed to fill or cover orifice. In another exemplary embodiment of a hybrid valve the skin itself can serve as one of the flow control layers.

Wick Permutations

Figure 11A:
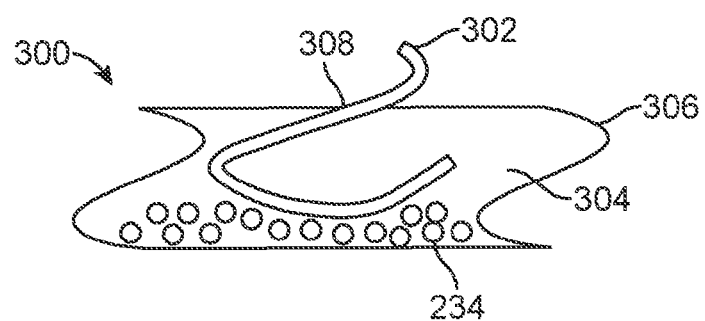
FIG. 11A illustrates another variation of a device having a fluid transport member that comprises a fluid wick that extends into a reservoir of the device.

FIG. 11A illustrates another variation of a device 300 having a fluid transport member that comprises a fluid wick 302 that extends into a reservoir 304 of the device 300. Typically, a fluid wick structure conveys fluids from a wet end to a dry (or "drier") end by capillary action. For example, if one end of liquid wick structure 302 is immersed in a liquid whilst the other end of liquid wick structure 302 is disposed in air, then the liquid moves through the wick structure 302 from the immersed end to the "in-air" end, at which end, typically, it will be absorbed by a filler material. The liquid will continue to flow through the liquid wick structure until such time that the "in-air" end is also immersed in liquid (that is, typically, immersed in a puddle of accumulated fluid).

Liquid wick structure 302 can optionally comprises a strip or thread of water absorbent material, for example, an absorbent matrix of cotton pulp (e.g. as in a sanitary napkin), polyvinyl acetal (e.g., as in an eye wick), polyvinyl alcohol sponge (e.g., as in ear wicks), or other materials typically used in, for example, surgical sponges. Alternatively, liquid wick structure 302 can comprise a strip or multi-strand thread of non-water-absorbing material, for example capillary-channeled nylon or polyester, wherein small capillaries are formed between the interior walls of the non-absorbent material. The wick can also comprise oxidized cellulose (available from Jinan Vincent Medical Products Co., Ltd, 122# East Toutuo Street Huangyan, Jinan, Shandong, China). Oxidized cellulose is known to absorb water but, as it is a polysaccharide, eventually solubilize after prolonged immersion in water.

In one variation, a wick structure 302 can have a substantially circular cross-section, the cross-section generally being greater than 2 mm in diameter and less than 8 mm in diameter, although both greater and smaller diameter wicks may be appropriate for large or small constructs respectively, the limits being determined by practicality and convenience rather than functionality.

Wick structure 302 is designed to convey fluid from the exterior to the interior of device 300, through an orifice in material surface 306; its length is preferably the sum of a convenient exterior segment, perhaps 2 cm, and an interior segment SKG2100 that is long enough to reach from orifice 308 to the furthest interior space in which filler material may be disposed. For some variations of the device, an interior segment of the wick 302 is approximately 6 cm, so a typical liquid wick structure 302 can be up to approximately 8 cm long. In other embodiments liquid wick structure 302 is between 4 cm and 12 cm in length. However, any range of wick length is within the scope of this disclosure.

In one variation, liquid wick structure 302 is inserted through an orifice 308 in device 300, where the device 300 is otherwise impermeable to fluid. Orifice 308 can be designed with a diameter that is approximately 50% of the diameter of liquid wick structure 302 to ensure that liquid wick structure 302 fits tightly and securely into orifice 308 when liquid wick structure 302 is dry. In some embodiments, orifice 308 may also have a diameter that is less than 50% of the diameter of liquid wick structure 302. The minimum diameter for orifice 308 is limited by constriction of the capillary action in liquid wick structure 302. That is, depending on the internal structure of liquid wick structure 302 and its material properties, too small an orifice will substantially shut off the transmigration of fluid through the liquid wick structure.

Alternatively, in some embodiments, orifice 308 may have a diameter that is greater than 50% of the liquid wick structure diameter, particularly if liquid wick structure 302 is being securely held by other means. With a large (greater than 50% orifice of the liquid wick structure diameter), liquid wick structure 302 can be heat-sealed, glued, or otherwise affixed in place in orifice 308 to prevent it from being displaced from its operational disposition.

Figure 11B:
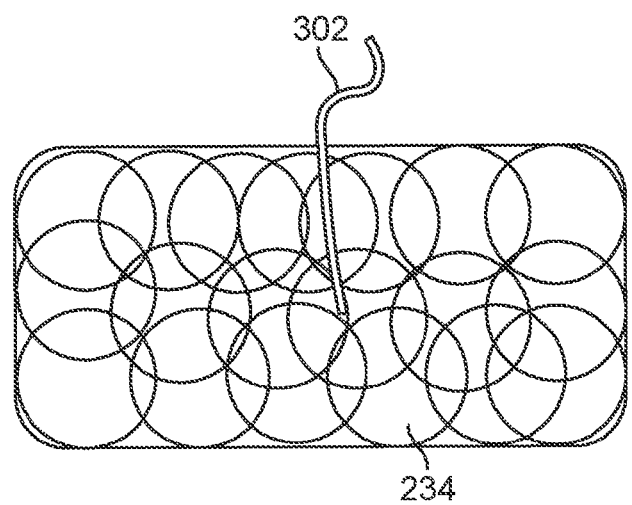
FIG. 11B shows the exterior segment of liquid wick structure immersed in a liquid causing liquid to be drawn into the absorbent wick material of liquid wick structure and further drawn from the wet wick.

As illustrated in FIG. 11B, when the construct, or at least the exterior segment of liquid wick structure 302 is immersed in a liquid, liquid is initially drawn into the absorbent wick material of liquid wick structure 302 and is further drawn from the wet wick material toward the dry wick material until interior segment of liquid wick structure 302 is substantially saturated. Liquid, on reaching the surface of liquid wick structure 302 (and in particular the end of interior segment), can be shed by dripping or it may be drawn off by contact with the absorbent, dry filler material. Filler material 306 swells as it absorbs liquid. The predetermined quantity of dry filler material, when fully expanded, fills the construct to a slightly positive pressure and surrounds interior segment in a hydrated mass 234. This mass is the functional equivalent of a liquid bath. With both ends of liquid wick structure 302 are immersed in fluid, the liquid wick structure's capillary action stops or slows considerably, thereby ending fluid movement between the exterior and the interior of construct 300.

Figure 12A:
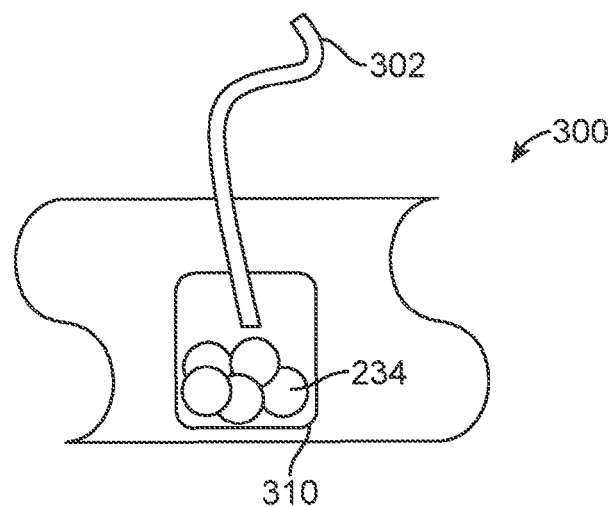
FIG. 12A, shows an exemplary embodiments of liquid wick structure fluidly coupled to a secondary, interior bag, pouch, or other container.

As illustrated in FIG. 12A, some exemplary embodiments of liquid wick structure 302 is fluidly coupled to a secondary, interior bag, pouch, or other container 310 to ensure that interior segment of the wick 302 is in direct contact with filler material 234 located within the container 310.

As filler material 234 swells, the container 310 releases filler material 234 into the reservoir of the device 300, where it continues to receive hydration from liquid wick structure 302. In one embodiment, illustrated in FIG. 12A, secondary bag 310 is water soluble, dissolving quickly as the partially hydrated hydrogel swells within it. In other embodiments secondary bag 310 comprises one or more weakened seams, the weakened seams splitting open as the hydrogel swells against it. In yet other embodiments, the entire secondary bag 310 comprises a structurally weak, permeable material, unable to contain the pressure of the swelling hydrogel. In yet other embodiments, secondary bag 310 comprises seams closed with sutures, the sutures being either inherently weak or water soluble. Any portion of a wick can be coupled to a container, not just the ends of the wick. For example, a wick can be folded such that the folded end is positioned within the container.

The wick 302 can be held in place within the container 310 as described above for the orifice. Alternatively it may be sealed closed by heat-sealing, gluing, or other means so that the tip of interior segment is disposed in direct contact with filler material 234.

In some embodiments, liquid wick structure 302 may be fabricated from a material that dissolves or degrades in liquid comparatively slowly relative to the time it takes for the filler material to fully expand. The material selected for this embodiment maintains its integrity and wicking ability long enough to fully hydrate filler material 234 but then degrades and disappears once the filler material is fully expanded. Examples of such materials include thin, cellulose-derived, porous woven or nonwoven materials and 'ropes' made of smaller tubes, including combinations of nanotubes.

Figure 12B:
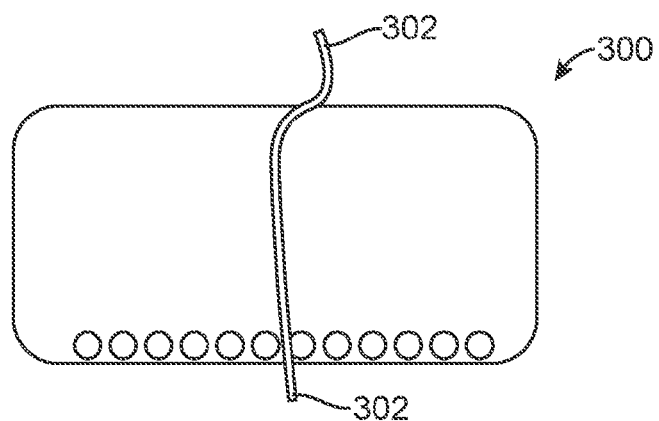
FIG. 12B illustrates another embodiment of a device having multiple liquid wick structures.

FIG. 12B illustrates another embodiment of a device 300 having multiple liquid wick structures. This embodiment comprises a dual wick structure in which a single wick structure 302 delivers fluid into the reservoir through both ends. As shown, a wick is threaded through both sides of the skin of the device so that the wick is exposed on both sides. These two exterior wick segments absorb fluid and convey the fluid between an exterior of the device and the reservoir. Clearly, two or more wick structures can be used rather than both ends of a single wick structure.

Figure 12C:
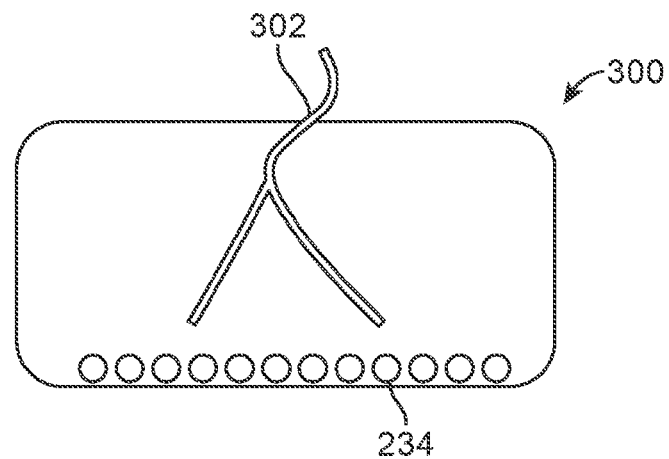
FIG. 12C, shows an interior segment of a single liquid wick structure that is divided into two or more sub-segments.

As shown in FIG. 12C, in other embodiments the interior segment of a single liquid wick structure 302 is divided into two or more sub-segments. Sub-segments of the wick structure 302 can be directed to different locations in the reservoir of the device to distribute hydration fluid 1105 more efficiently or, as discussed above, each end can be directed to a secondary container.

Figure 12D:
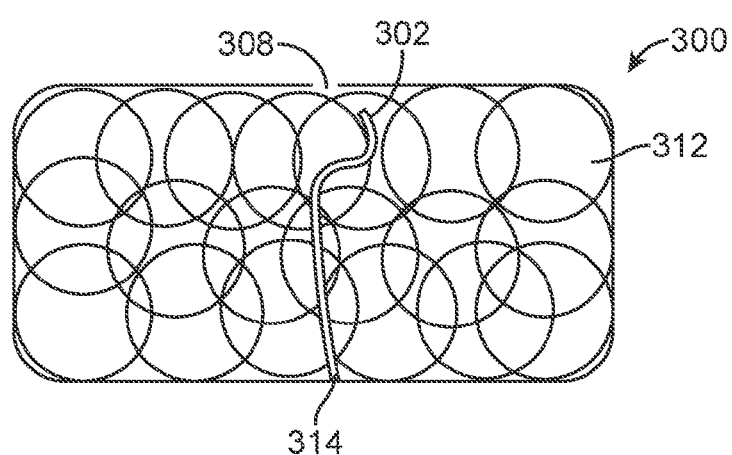
FIG. 12D shows a wick structure affixed to a portion of the interior of the reservoir.

In another aspect, a wick structure 302 can be affixed to a portion of the interior of the reservoir as illustrated in FIG. 12D. As shown above, the wick initially extends outside of the device. Upon swelling of the filler material, as the device expands, the section of the wick that is initially outside the device is pulled into the interior of the device assembly because it is affixed or secured to the interior of the reservoir.

Clearly, variations of the wick structure can be combined with other aspects and features described herein. Moreover, any embodiment disclosed herein can be combined with aspects of alternate embodiments or with the embodiment itself. For example, the wicks described herein can be combined with the valve mechanisms described herein and/or can be combined with the release materials discussed throughout this specification.

Figure 13A:
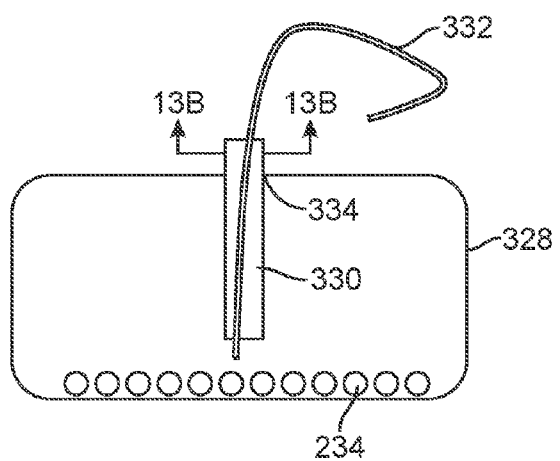
FIG. 13A illustrates a variation of a tunnel valve as discussed above that forms a sealable fluid path preventing material from escaping from the interior of the device.

FIG. 13A illustrates a variation of a tunnel valve as discussed above. As shown, the tunnel valve forms a sealable fluid path that prevents material from escaping from the interior of the device. FIG. 13A illustrates an example of a device with a tunnel valve forming the sealable fluid path. As shown, device assembly 326 contains a valve member 330 comprising a fluid impermeable material that can be securely joined to the skin 328 in any manner conventionally known or by those discussed herein (including, but not limited to gluing, welding, heat sealing, or other means). Examples of materials useful for the tunnel valve include polyurethane, nylon-12, and polyethylene. The tunnel valve 330 can include any number of fluid transport members 332. In the illustrated variation, the valve is coupled to a conduit. However, variations include a wick type device located within the tunnel valve.

Figure 13B:
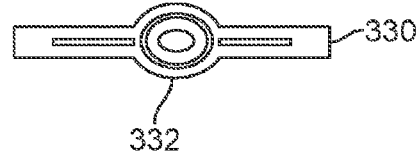
FIG. 13B shows a cross sectional view of tunnel taken along line 13B-13B of FIG. 13A.
Figure 13C:
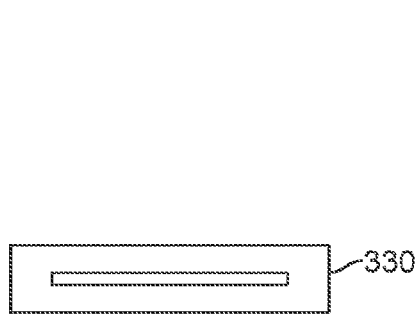
FIG. 13C shows the tunnel closing.

FIG. 13B shows a cross sectional view of tunnel 330 taken along line 13B-13B of FIG. 13A. As shown the tunnel valve 330 forms part of the fluid transport member 332 allowing transport of fluids between the interior/reservoir and interior of the device assembly. In certain variations, the tunnel valve 330 can be detachable from the remainder of the fluid transport member 332. Upon removal, the layers of the tunnel valve 330, as shown in FIG. 13C, close to an extent that the tunnel valve effectively closes and prevents migration of the filler material from the reservoir. In certain variations, the tunnel valve 330 fully closes, while in other variations, the tunnel 330 can remain slightly open. Variations of tunnel valves include assemblies of an extruded tube or two layers that are joined by gluing, welding, heat sealing, or other means at their two edges. In some variations, the tunnel valve has a wall thickness between 0.001" and 0.1". One example of a tunnel valve included a thickness of 0.0015". In additional variations, tunnel valves can be flexible, compressible and/or deformable. In additional variations, layers of the tunnel valve can be reopened by the passage a structure (e.g., a conduit or other fluid transport structure).

As noted above, the tunnel valve allows for detachment of the remainder of the fluid transport member at any time, but typically once a sufficient amount of fluid is delivered to the device. Removal can occur via applying tension to a portion of the fluid transport member. Variations of the tunnel valve can employ permeable membranes, filter, or valves placed at the end of the tunnel valve to prevent dry hydrogel or other filler materials from entering the tunnel and affecting the ability of the tunnel valve to seal. In some embodiments, the membrane or filter may comprise a permeable fabric such as polyester, nylon, or cellulose. In other embodiments, a valve is placed at the end of tube comprised of a one-way duckbill or umbrella valve (available from MiniValve of Oldenzaal, Netherlands). Alternatively, or in addition, filler material 234 can be contained in a container as discussed above, which prevents the filler material from entering the tunnel valve and swelling upon infusion of liquid, thereby clogging the valve.

Delivery System

Figure 14:
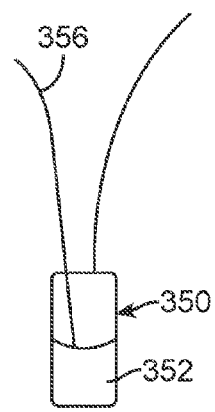
FIG. 14 shows a device assembly compressed to fit within an oral dosage form such as a pill, capsule, sleeve, or other form that enhances the ability of positioning the device via ingestion or swallowing without the aid of another medical device.

As shown in FIG. 14, in certain variations, the device assembly can be compressed to fit within an oral dosage form 352 such as a pill, capsule, sleeve, or other form that enhances the ability of positioning the device via ingestion or swallowing without the aid of another medical device. In such a case, the device 350 is contained within the oral dosage form 352 and can optionally include a tether 356. It should be noted that the conduits described above can also be used as a tether or vice versa. In any case, the tether 356 allows for controlling the deployment location of the device 350 within the gastrointestinal tract by manipulation of the tether 356, and finally completing the administration procedure by releasing control of the device 350, either by releasing the tether 356 for the patient to swallow or, more typically, by detaching the tether from the device 350 or oral dosage form. FIG. 14 also shows a tether 356 as having two ends to allow for greater control in positioning the device 350.

In accordance with the delivery method, a medical practitioner, typically a medically trained agent such as a physician, physician's assistant, or nurse, administers the tethered, encapsulated payload to a mammal, herein referred to as the patient. The method comprises the simultaneous steps of directing the patient to swallow oral dosage form while controlling the tether. In some embodiments controlling the tether comprises the use of a tube to transport liquid into the device, the method also includes infusion of liquid through the tube using a syringe, pump, or other liquid delivery means. Generally, the step of controlling the tether comprises, firstly, ensuring that the tether's proximal end is retained exterior to the patient and, secondly, assisting the patient by feeding the tether into the patient's mouth and throat at a rate compatible with the ingestion of the oral dosage form 352. That is, the agent typically adjusts the feed rate of the tether so the progress of the oral dosage form 352 down the esophagus is not impeded by tether-induced drag while at the same time the patient does not feel the tether is accumulating in his or her mouth. In additional variations, the medical practitioner can also use the tether by securing the section of the tether located outside of the patient's body (i.e., to a fixture in the room or to a part of the patient).

The method further comprises an optional step of controlling the delivery distance of the device. The delivery distance is, essentially, how far into the gastrointestinal tract the device is permitted to travel. Typical devices are designed to be deployed in the stomach although some devices may be designed to reach only the esophagus whilst other devices can be intended to reach the pylorus or beyond. The step of controlling the delivery distance is best accomplished with a device attached to a marked tether, whereby the length of the ingested tether corresponds to the instantaneous delivery distance, which length being directly readable from a marked tether. Part of this optional step of controlling the delivery distance is stopping the further ingestion of the tether.

In certain variations, the oral dosage form 352 dissolves upon reaching the stomach and the fluids therein. Once free from the oral dosage form, the device 350 is free to expand into deployed state or an active profile. Alternatively, device 350 expands into its active profile upon infusion of a hydrating fluid through the fluid transfer member.

Filler Material Release

One of skill in the art will note that the human GI tract is unique among the abdominal viscera as it is periodically exposed to very cold and hot substances during routine alimentation. For instance, the temperature of the stomach is known to increase to 44° C. after ingestion of a hot meal heated to 58° C. but quickly return to core body temperature (37-39° C.) in 20 minutes. Moreover, the temperature of the stomach can reach as high as 48° C. for between 1-2 minutes if 500 milliliters of 55° C. tap water is consumed rapidly (under 2 minutes) on an empty stomach. Thus, a biocompatible material that could be eliminated by melting would ideally remain stable at core body temperature (37-39° C.) but melt in response to a planned intervention that raised the temperature in the vicinity of the biocompatible material to the material's melting point. In the GI tract, such a material would have to withstand daily fluctuations in gastric temperature (e.g. after ingestion of a hot meal) and remain stable at temperatures between 37° C. and 44° C. but melt in response to a planned intervention (e.g. consuming 500 milliliter of 55° C. tap water).

In some examples it was noted that one material, polycaprolactone (PCL), has been extruded into a strong monofilament (Japanese publication JP-A05-59611 A) and has a natural melting point of 60° C., a melting point that is probably not safely usable in human stomachs. However, PCL can be modified to lower its melting point to more physiologically acceptable temperature. Moreover, the modified polymer can still be extruded into a strong monofilament suitable for suturing and stitching or a film suitable for heat welding to a membrane. PCL filamentary material with reduced melting temperatures ($T_M$) is available from Zeus Industrial Products of Orangeburg, S.C., wherein 60° C.>$T_M$>45° C. by specification.

Delivery of Thermal Exogenous Substance

In some variations the degradable material used as release material 106 is allowed to degrade at its natural degradation rate in the mammalian gastric environment. In other variations, degradation is triggered or effected by the intentional introduction of an exogenous substance 120. In additional embodiments, exogenous substance 120 is introduced orally and at least partially in a liquid format into the stomach. In the stomach, the exogenous substance 120 mixes with the resident gastric fluid to become an immersing fluid that substantially bathes the construct. Alternatively, the exogenous substance 120 may be introduced into the stomach in a solid state, as in a tablet or capsule, typically accompanied by a liquid, whereby the solid is dissolved and becomes the immersing fluid, particularly when mixed with gastric fluids. In certain embodiments extra-corporal stimulation of the exogenous substance 120 may be used.

In many variations, the release material comprises modified PCL material, either as a thin film for degradable patch or as a filamentary material. In general, modified PCL melts at a specified melting temperature, $T_M$ and the temperature of the stomach, $T_S$, remains below $T_M$. The exogenous agent for PCL, therefore, comprises an elevated temperature liquid—at temperature $T_L$—which raises $T_S$ above $T_M$. The exogenous agent temperature $T_L$ needed to raise $T_S$ above $T_M$ is based on the design details of entire system; that is, the means of delivery of exogenous substance 120, the design of release material (that is, for example, stitches, patch or knot), and the specified melting temperature, $T_M$, of the modified PCL.

For example, an intragastric construct comprising $T_M=48°$ C. modified PCL will degrade after the rapid ingestion of a large volume of water with $T_L=55°$ C. Clearly, the location of the PCL release material may affect the rate and/or temperature at which the PCL degrades. The extra-corporal exogenous substance 120 temperature $T_L$ is higher than the melting temperature of the PCL to account for cooling of the formulation during transit to the stomach and due to mixing with the existent stomach fluids and for the placement of the release material. In one example, it was found that the rapid ingestion of approximately 500 milliliter of 55° C. water elevates stomach temperature $T_S$ to at least 48° C., high enough to dissolve/degrade the modified PCL and allow the device to open and release its hydrogel contents.

In another example, an intragastric construct comprising with $T_M=50°$ C. modified PCL will degrade after rapid endoscopic infusion of 500 milliliter tap water with $T_L=65°$ C., a temperature that is too hot for comfortable oral ingestion but which is tolerated by the stomach when the liquid is delivered directly to the stomach. Alternatively, the exogenous substance 120 may be delivered directly to the stomach via a nasogastric tube, again circumventing the comfort limitations of oral ingestion.

In another variation, an exogenous substance can be used to raise the temperature or otherwise change the conditions of bodily fluids to effect release of the device. Additional variations allow for the use of an exterior energy source to raise the temperature of the area surrounding the device. For example, a patient can ingest a sufficient volume of fluid, followed by the application of an external energy source (e.g., radiofrequency or ultrasound) to the exterior of the patient's abdomen to warm the fluid within the stomach to the desired $T_M$. In another variation, the exogenous substance, e.g. elemental magnesium, itself causes an exothermic reaction to occur in the stomach.

Yet another approach providing a exogenous substance 120 to an intragastric device comprising $T_M=50°$ C. modified PCL is the ingestion of 500 mL of alkaline solution (e.g. saturated sodium bicarbonate) pre-warmed to 55° C. Said solution initiates an exothermic reaction upon neutralization with the stomach acid, warming the stomach contents above the 50° C. PCL melting point.

Emptying and Deswelling Degradation

Certain embodiments of the present invention comprise a system for the rapid degradation and volume reduction of an intragastric hydrogel-containing medical device. The system disclosed herein consists of three paired materials: a degradable device structural element, a hydrogel and a tuned dissolution (or deswelling) solution selected to degrade the structural element and deswell the particular hydrogel according to their underlying chemical properties. The system is employed in the following way: First, an intragastric device containing a hydrogel is swallowed, ingested or inserted into a patient's stomach. The hydrogel swells when exposed to fluid and takes up space within the stomach lumen. Following a sufficient residence time determined by the patient or by an administering healthcare professional, a hydrogel deswelling agent is ingested by or administered to the patient. The deswelling agent (which may be in the form of a solid, liquid, or gas) causes the device to release the enclosed hydrogel by degrading a structural element (a stitch, a line of stitches, a seam, a glue, a patch, a plug, or other known structural elements in the art). The deswelling agent then rapidly decreases the volume of the hydrogel to facilitate pyloric passage and safe distal GI tract transit.

Numerous structural elements susceptible to degradation following exposure to particular aqueous conditions are known in the art. Examples include the polymer polycaprolactone which can be extruded into plaques, films, monofilaments, plugs, and other structural elements. Polycaprolactone (available from The DURECT Corporation, Birmingham, Ala.) has a melting temperature of approximately 60° C. and can be thermoformed, molded, or extruded into a number of structural elements known in the art. Modified PCL with melting temperatures ranging from ~40-60° C. (available from Zeus Industrial Products of Orangeburg, S.C.) can also be thermoformed, molded, or extruded into a number of structural elements known in the art.

Device structural elements can also be produced from materials that selectively dissolve when exposed to elevated pH conditions, but remain substantially structurally intact when exposed to lower pH conditions. For example, stretch-drawn fibers can be produced from poly(methacrylic acid-co-methyl methacrylate), available as EUDRAGIT S-100, or poly(methyl acrylate-co-methyl methacrylate-co-methacrylic acid) co-polymer, available as EUDRAGIT FS-30D, both from Evonik Industries of Darmstadt, Germany. These polymers can be formulated with Tri Ethyl Citrate (TEC) and extruded into filaments which can be used to close the seams of an intragastric device. For example, a 70% EUDRAGIT S-100 and 30% Tri Ethyl Citrate (available from Samrudhi Pharmachem of Mumbai, India) mix can be blended and extruded into fiber using a single screw extruder. The resulting filament can then be used to sew a seam of an intragastric device filled with hydrogel. The resulting fiber and seam remain substantially structurally stable (for example, having mechanical properties such as strength which do not change over time) but rapidly degrade (for example, by dissolving) at a pH greater than about 7.

Some hydrogels may be deswelled by exposure to an aqueous solution comprising elevated salt concentrations. FIG. 15 illustrates this deswelling effect and shows the degree of swelling for several cross-linked polyacrylic acid and cross-linked polyacrylamide hydrogels after exposure to solutions containing various solutes at various concentrations. Each subject hydrogel was loaded into a permeable polyester mesh pouch and exposed sequentially to the listed environments.

Pouches were created from 9.5 cm×22.0 cm pieces of polyester mesh (available as China Silk from Ryco of Lincoln, R.I.), folded in half along the long edge, closed along the long edge and one short edge with fabric glue (available as Bish's Tear Mender from True Value Hardware of Cambridge, Mass.), and filled with 1.0 gram of one of the following superabsorbent hydrogels: Waste Lock 770 (available from M2 Polymer Technologies, Inc.), Waste Lock PAM (available from M2 Polymer Technologies, Inc.), Tramfloc 1001A (available from Tramfloc of Tempe, Ariz.), Water Crystal K (available from WaterCrystals.com), Hydrosource (available from Castle International Resources of Sedona, Ariz.), poly(acrylamide-co-acrylic acid) potassium salt (available from Sigma-Aldrich), and Soil Moist (available from JRM Chemical of Cleveland, Ohio). The pouches were closed along the remaining short edge with three square knots of a polyester sewing thread, weighed, placed in a beaker filled with 350 mL tap water, and incubated at 37 C for 1 hour. The pouch was weighed after 30 minutes and 1 hour in tap water. The pouch was then submerged in a beaker incubated at 37 C containing 350 mL of 2% sodium chloride, blended dog food (150 grams of Adult Advanced Fitness Dry Dog Food from Hill's Science Diet blended in 50 mL simulated gastric fluid [2 grams sodium chloride, 3.2 grams pepsin, 7 mL hydrochloric acid, brought to 1 liter with tap water], and brought to 1 L with tap water), pH 3 buffer (available as Hydrion pH 3 buffer from Micro Essential Laboratory of Brooklyn, N.Y.), and 2.5% calcium chloride for 3.5 hours each. In between each of these incubations, the pouches were submerged in a beaker containing 350 mL tap water incubated at 37 C. The pouch was weighed after each incubation. The pouches became lighter after each incubation in the different media but regained most of their mass after incubation in tap water. However, in 2.5% calcium chloride, each pouch lost a significant amount of mass and could not regain this mass after incubation in tap water (data not shown).

Figure 15A:
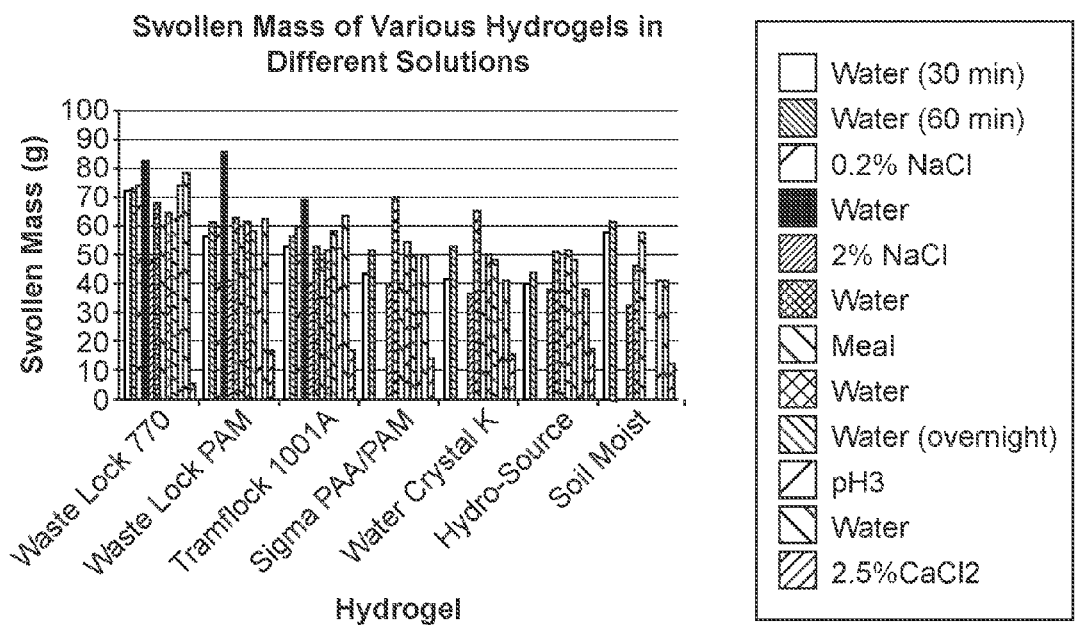
FIG. 15A shows hydrogels comprised of either cross-linked polyacrylic acid or cross-linked polyacrylamide, materials that are widely used in medical device applications.

The hydrogels shown in FIG. 15A are comprised of either cross-linked polyacrylic acid or cross-linked polyacrylamide, materials that are widely used in medical device applications. As evidenced by this data, administration of a deswelling solution comprised of 2.5% Calcium Chloride could rapidly decrease hydrogel volume by ten times or more. Therefore, any of the hydrogels disclosed in FIG. SGL7 paired with a 2.5% Calcium Chloride deswelling solution constitute a system for ionic strength-based construct degradation.

Figure 15B:
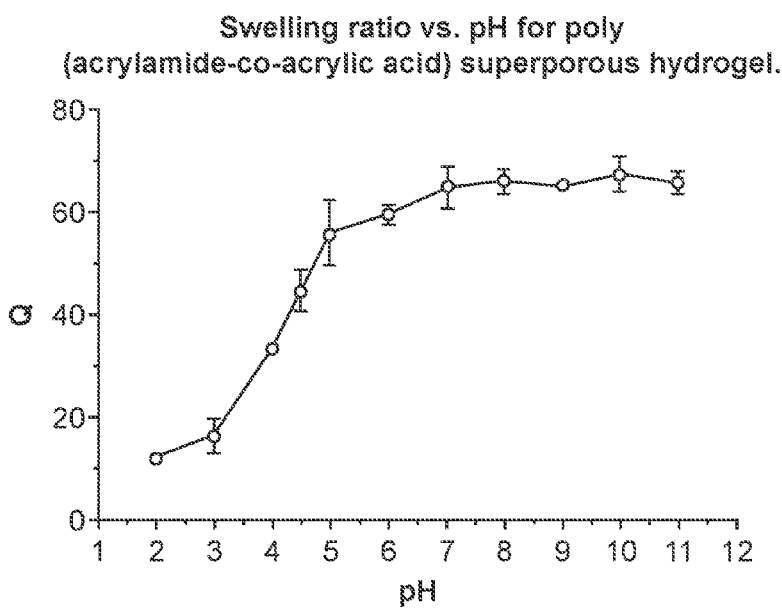
FIG. 15B shows cross-linked polyacrylic acid or cross-linked polyacrylamide, materials that are widely used in medical device applications.

The hydrogels shown in FIG. 15B are comprised of either cross-linked polyacrylic acid or cross-linked polyacrylamide, materials that are widely used in medical device applications. As evidenced by this data, administration of a deswelling solution comprised of 2.5 The composition and fabrication of this hydrogel is reported in the literature (Gemeinhart, et al., 2000). As evidenced from the data, swelling extent of this hydrogel rapidly increases above pH 3. This hydrogel is comprised of highly biocompatible materials and is therefore suitable for ingestion by a patient as part of a space occupation device. The hydrogel will swell in a normal gastric environment. When the device is ready to be eliminated, a low pH deswelling solution could be administered to the patient to rapidly de-swell the hydrogel.

Figure 15C:
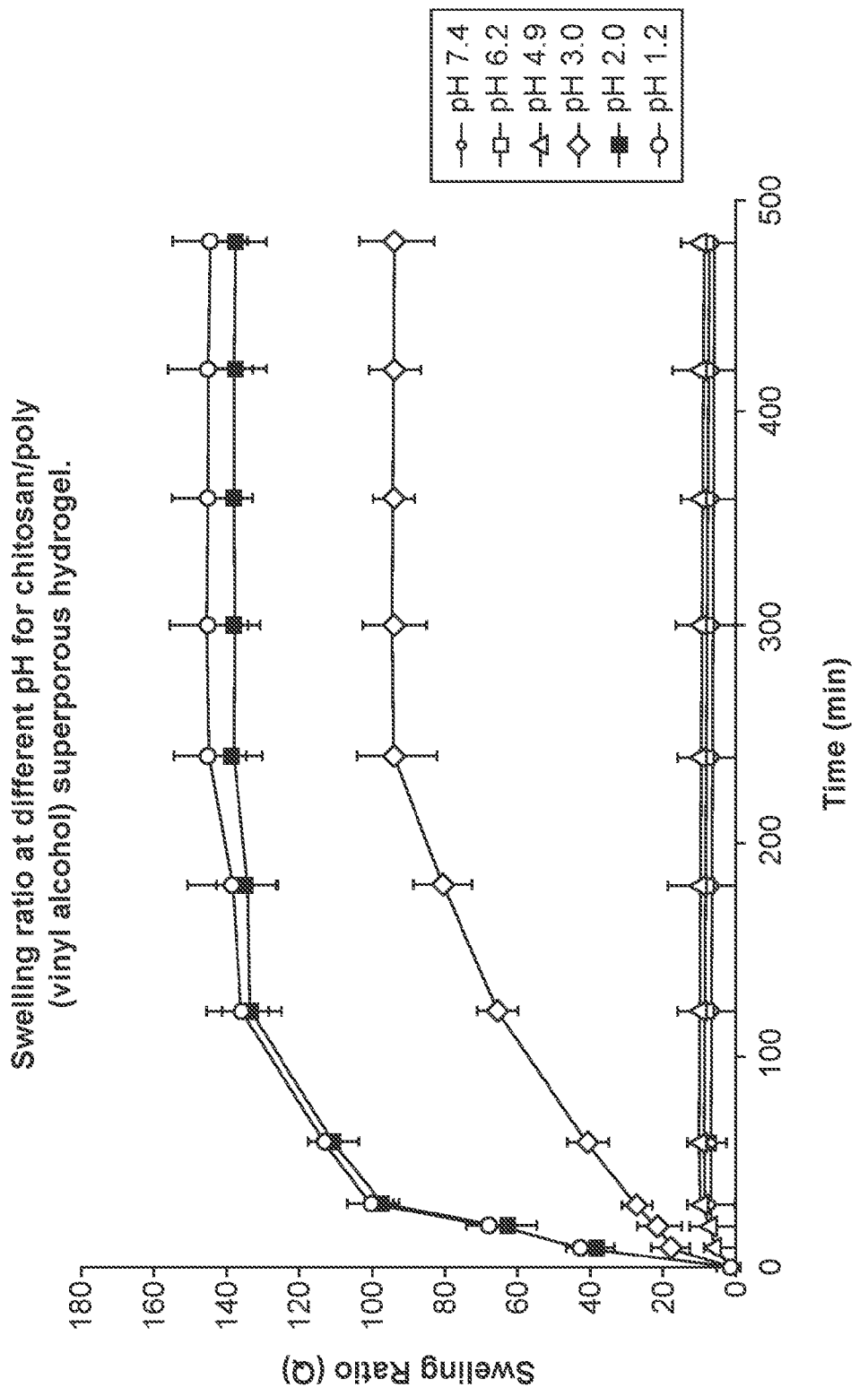
FIG. 15C depicts the swelling performance of a chitosan/poly(vinyl alcohol) superporous hydrogel in solutions at different pHs.

FIG. 15C depicts the swelling performance of a chitosan/poly(vinyl alcohol) superporous hydrogel in solutions at different pHs. The composition and fabrication of this hydrogel is reported in the literature (Gupta, et al., 2010). As shown in the FIG. 15C, the swelling extent of this hydrogel rapidly decreases above pH 3. This hydrogel is comprised of highly biocompatible materials and could be swallowed by a patient as part of a space occupation device. This hydrogel is swollen with a solution at low pH (below 3). When the device is ready to be eliminated, an elevated pH deswelling solution (pH>3) is administered to the patient to rapidly de-swell the hydrogel.

Exemplary Embodiment 1: One Embodiment of the System for Rapid Hydrogel construct degradation comprises a hydrogel-containing intragastric device and deswelling agent capable of simultaneously opening the device and deswelling the hydrogel. The construct in this exemplary embodiment is fabricated using the following materials: Pouches are created from 9.5 cm×22.0 cm pieces of polyester mesh (available as China Silk from Ryco of Lincoln, R.I.), folded in half along the long edge, closed along the long edge and one short edge with fabric glue (available as Bish's Tear Mender from True Value Hardware of Cambridge, Mass.), and filled with 1.0 gram of Waste Lock 770 hydrogel (available from M2 Polymer Technologies, Inc.). The pouch(es) are closed along the remaining short edge with, for example, three square knots of modified Polycaprolactone thread (available from Zeus Industrial Products of Orangeburg, S.C.) processed to melt at 47° C. The corresponding dissolution solution comprises a 2.5% Calcium Chloride aqueous solution heated to 55° C. This solution degrades the modified polycaprolactone structural element (knots holding the pouches closed) and deswells the salt-sensitive hydrogel.

Additional Exemplary Embodiments: Additional exemplary embodiments of the system for rapid hydrogel construct degradation are fabricated in a similar manner to exemplary embodiment 1. The different embodiments comprise different combinations of "device material", that is, the thread used to close the pouches, hydrogel material, and dissolution formulation. The table below, discloses these combinations. The following combinations are for illustrative purposes only and are not meant to be limiting unless specifically claimed.

| Polymer | Type | Degradation Mode | Degradation Condition | Degradation Time |
|---|---|---|---|---|
| Poly(glycolic acid) | Bioabsorbable | Gradual hydrolysis | Exposure to water or acid | 2-3 months |
| Poly(dioxanone) | Bioabsorbable | Gradual hydrolysis | Exposure to water or acid | 6-8 months |
| Poly(lactic-co-glycolic acid) | Bioabsorbable | Gradual hydrolysis | Exposure to water or acid | 2 months |
| Poly(vinyl alcohol) | Bioabsorbable | Rapid dissolution | Exposure to any aqueous solution | Seconds |
| Methyacrylic acid methyl-methacrylate co-polymers | Bioabsorbable | Hydrolysis; on-demand pH-dependent dissolution | Exposure to alkaline pH | Days at near neutral pH and minutes to hours at alkaline pH |

-continued

| Polymer | Type | Degradation Mode | Degradation Condition | Degradation Time |
|---|---|---|---|---|
| Poly(caprolactone) | Bioabsorbable | Hydrolysis; on-demand at temperatures greater than 60° C. | Exposure to heat | 6 months at temperatures less than melting point, seconds at or above melting point |
| Polyester | Non-bioabsorbable | None | None | N/A |
| Poly(propylene) | Non-bioabsorbable | None | None | N/A |
| Nylon | Non-bioabsorbable | None | None | N/A |

The invention claimed is:

1. A device for temporarily occupying a space within a patient's body, the device comprising:
a device assembly comprising a reservoir, the device assembly having a deployment profile and an active profile, where the deployment profile is smaller than the active profile and permits deployment of the device assembly within a space in the patient's body, where delivery of a fluid into the reservoir causes expansion of the device assembly towards the active profile;
where an extension of the device assembly that extends into the reservoir to form a release channel where the extension forms an elongate structure extending beyond an internal seam of the device assembly;
a release material located within the reservoir and coupled to the release channel while spaced from the internal seam to prevent fluid flow therethrough; and
wherein exposure of the release material to the fluid reduces a structural integrity of the release material, such that degrading of the release material allows fluid flow through the release channel permitting fluid to exit the reservoir.

2. The device of claim 1, wherein a portion of the extension of the device assembly extending into the reservoir separates the release material from the release channel such that the release material remains entirely physically separated from an environment within the patient's body until reduction of the structural integrity of the release material allows fluid flow through the release channel.

3. The device of claim 1, further comprising an energy storage element located within the release channel that expands reduction of the structural integrity of the release material.

4. The device of claim 1, where the extension of the device assembly extending into the reservoir comprises a material that is attached to an exterior surface of the device assembly.

5. The device of claim 1, where the extension of the device assembly extending into the reservoir comprises an exterior surface of the device assembly.

6. The device of claim 1, where an exterior surface of the device assembly is fluid impermeable.

7. The device of claim 1, where the release material comprises a structure selected from the group consisting of a suture, staple, filament, clip, band, and cap.

8. The device of claim 1, where the release material comprises a mechanical closure.

9. The device of claim 1, where in the deployment profile, the device assembly is configured to fit within an oral dosage form selected from a group consisting of a pill, capsule, and sleeve.

10. The device of claim 1, where in the active profile the device assembly comprises an oblate spheroid shape.

11. The device of claim 1, further comprising a conduit extending from an exterior of the device assembly through a valve and into the reservoir, where the conduit permits delivery of the fluid into the reservoir allowing the device assembly to assume the active profile, wherein the conduit is slidably detachable from the valve such that removal of the conduit causes the valve to seal and prevent the fluid from escaping from the reservoir through the valve.

12. The device of claim 11, where the conduit remains within an interior of the valve when positioned within the reservoir.

13. The device of claim 1, where the release material is located on a surface of the device assembly.

14. The device of claim 1, further comprising an expandable material located within the reservoir.

15. The device of claim 1, where a volume of the device assembly is at least 300ml in the active profile.

16. The device of claim 11, where the valve extends beyond an exterior surface of the device assembly.

17. The device of claim 1, further comprising a swellable filler material in the reservoir.

18. The device of claim 1, where the device assembly can be reduced to at least a 5ml volume when in the deployment profile.

19. The device of claim 11, where the conduit extends beyond the valve into the reservoir.

20. The device of claim 1, where the extension extends from the internal seam of the device assembly towards a center of the reservoir.

21. The device of claim 1, where the extension extends from an interior wall of the device assembly towards a center of the reservoir.

22. The device of claim 1, where the release material is spaced from an interior wall of the device assembly.

* * * * *